US009499823B2

(12) United States Patent
De Lorenzo et al.

(10) Patent No.: US 9,499,823 B2
(45) Date of Patent: Nov. 22, 2016

(54) CONSTRUCTS EXPRESSING CHIMERIC RECEPTORS AND USE THEREOF FOR THE CONTROLLED ACTIVATION OF DEFENCE RESPONSE TO PATHOGENS IN PLANTS

(75) Inventors: Giulia De Lorenzo, Rome (IT); Felice Cervone, Rome (IT); Alexandre Brutus, Rome (IT); Francesca Sicilia, Rome (IT)

(73) Assignee: UNIVERSITA DEGLI STUDI DI ROMA "LA SAPIENZA", Rome (IT)

( * ) Notice: Subject to any disclaimer, the term of this patent is extended or adjusted under 35 U.S.C. 154(b) by 1356 days.

(21) Appl. No.: 13/375,705

(22) PCT Filed: Jun. 4, 2010

(86) PCT No.: PCT/EP2010/057845
§ 371 (c)(1),
(2), (4) Date: Jul. 25, 2013

(87) PCT Pub. No.: WO2010/139790
PCT Pub. Date: Dec. 9, 2010

(65) Prior Publication Data
US 2012/0137392 A1    May 31, 2012

(30) Foreign Application Priority Data
Jun. 4, 2009    (IT) .............................. RM2009A0279

(51) Int. Cl.
*C12N 15/62*   (2006.01)
*C12N 9/12*    (2006.01)
*C12N 15/82*   (2006.01)

(52) U.S. Cl.
CPC .............. *C12N 15/62* (2013.01); *C12N 9/1205* (2013.01); *C12N 15/8281* (2013.01); *C12N 15/8282* (2013.01)

(58) Field of Classification Search
CPC .............. C12N 9/1205; C12N 15/8282; C12N 15/8281
See application file for complete search history.

(56) References Cited

PUBLICATIONS

Shiu, Shin-Han, and Anthony B. Bleecker. "Plant receptor-like kinase gene family: diversity, function, and signaling." Science Signaling 2001.113 (2001): re22.*
Hématy, K., et al, Candice Cherk, and Shauna Somerville. "Host—pathogen warfare at the plant cell wall." Current opinion in plant biology 12.4 (2009): 406-413.*
Gómez-Gómez, Lourdes, and Thomas Boller. "FLS2: an LRR receptor—like kinase involved in the perception of the bacterial elicitor flagellin in Arabidopsis." Molecular cell 5.6 (2000): 1003-1011.*

(Continued)

*Primary Examiner* — Russell Kallis
*Assistant Examiner* — Weihua Fan
(74) *Attorney, Agent, or Firm* — Lucas & Mercanti, LLP

(57) ABSTRACT

The present invention relates to a construct able to express in at least one plant tissue, a chimeric receptor, said chimeric receptor being essentially made of the extracellular region, comprising the external juxtamembrane portion, of a first kinase receptor R1; and the transmembrane region and the intracellular region, comprising the internal juxtamembrane portion, of a second kinase receptor R2, wherein R1 and R2 are different and uses thereof.

7 Claims, 22 Drawing Sheets

(56) References Cited

PUBLICATIONS

He, Z., et al. "Perception of brassinosteroids by the extracellular domain of the receptor kinase BRI1." Science 288.5475 (2000): 2360-2363.*

Zhao, Jing, et al. "Dissection of the factors affecting development-controlled and race-specific disease resistance conferred by leucine-rich repeat receptor kinase-type R genes in rice." Theoretical and Applied Genetics 119.2 (2009): 231-239, published online on Apr. 24, 2009.*

Kohorn, Bruce D., et al. "An Arabidopsis cell wall-associated kinase required for invertase activity and cell growth." The Plant Journal 46.2 (2006): 307-316.*

Cao, Y., et al., "Functional analysis of Xa3/Xa26 family members in rice resistance to *Xanthomonasoryzae* pv. oryzae", Theoretical and Applied Genetics, vol. 115, No. 7, 2007, pp. 887-895, XP002561797 & Cao, Y., et al. : "Supplementary Data: Functional analysis of Xa3/Xa26 family members in rice resistance to *Xanthomonasoryzae* pv. oryzae"[Online] vol. 115, No. 7, 2007, XP002591616, Theoretical and Applied Genetics, Retrieved from the Internet: URL:http://www.springerlink.com/content/.

He, Z., et al.: "Perception of brassinosteroids by the extracellular domain of the receptor kinase BR11", Science, vol. 288, 2000, pp. 2360-2363, XP002561798.

\* cited by examiner

A

B

A

B

C 10 min 20 min

SEQUENCE LISTING

<160> NUMBER OF SEQ ID NOS: 42

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
atgcggatcc atgaagttac tctca                                              25

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
gcatggtacc ctacctagga acttctcgat cc                                      32

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
atgcggatcc atgaagctgt ccttttc                                            27

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
atcggaatcc atgaagctgt ccttttcac                                          29

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
gcatggtacc ctacctaggg catactatgt ag                                      32

<210> SEQ ID NO 6
<211> LENGTH: 41
<212> TYPE: DNA
<213> ORGANISM: Artificial Sequence
<220> FEATURE:
<223> OTHER INFORMATION: primer

<400> SEQUENCE: 6
attcttggat cagccgcggc tcttttgtta atcataattg t                41

<210> SEQ ID NO 7
<211> LENGTH: 41
<212> TYPE: DNA
<213> ORGANISM: Artificial Sequence
<220> FEATURE:
<223> OTHER INFORMATION: primer

<400> SEQUENCE: 7
acaattatga ttaacaaaag agccgcggct gatccaagaa t                41

<210> SEQ ID NO 8
<211> LENGTH: 40
<212> TYPE: DNA
<213> ORGANISM: Artificial Sequence
<220> FEATURE:
<223> OTHER INFORMATION: primer

<400> SEQUENCE: 8
ttctcgaaga gaaccagagt tgtcagtggt atttgtatag                  40

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
ctatacaaat accactgaca actctggttc tcttcgagaa                  40

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
atgcgaatcc atgaaggtgc aggaggg                                27

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
atgcccggga tgaaggtgca ggaggg                                 26

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
gcatggtacc ctacctaggg cggccagttt caatg                       35

<210> SEQ ID NO 13

<210> SEQ ID NO 13
<211> LENGTH: 42
<212> TYPE: DNA
<213> ORGANISM: Artificial Sequence
<220> FEATURE:
<223> OTHER INFORMATION: primer

<400> SEQUENCE: 13
ctgcaagcgt aaagagtttg cagttgtcag tggtatttgt at                42

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
atacaaatac cactgacaac tgcaaactct ttacgcttgc ag                42

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
gcctctgtca gttagaaaga aatggactac aattcttctt gg                42

<210> SEQ ID NO 16
<211> LENGTH: 42
<212> TYPE: DNA
<213> ORGANISM: Artificial Sequence
<220> FEATURE:
<223> OTHER INFORMATION: primer

<400> SEQUENCE: 16
ccaagaagaa ttgtagtcca tttctttcta actgacagag gc                42

<210> SEQ ID NO 17
<211> LENGTH: 46
<212> TYPE: DNA
<213> ORGANISM: Artificial Sequence
<220> FEATURE:
<223> OTHER INFORMATION: primer

<400> SEQUENCE: 17
ctttggggat gttccatgag aaggtaagtg ctgaagagct tcatag            46

<210> SEQ ID NO 18
<211> LENGTH: 47
<212> TYPE: DNA
<213> ORGANISM: Artificial Sequence
<220> FEATURE:
<223> OTHER INFORMATION: primer

<400> SEQUENCE: 18
ctatgaagct cttcagcact taccttctca tggaacatcc cccaaag           47

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19

| | |
|---|---|
| ggaagaagaa gacttacacc | 20 |

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20

| | |
|---|---|
| agtccacact taccacagta | 20 |

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21

| | |
|---|---|
| cgaaccctaa caacaaaaac | 20 |

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22

| | |
|---|---|
| gacgacacgt aagaaagtcc | 20 |

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23

| | |
|---|---|
| gtgaaagcac taggcgaagc | 20 |

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24

| | |
|---|---|
| atccgttcca gctagcatca | 20 |

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25

| | |
|---|---|
| tcgctggcat aacactatgg | 20 |

<210> SEQ ID NO 26
<211> LENGTH: 20
<212> TYPE: DNA

```
<213> ORGANISM: Artificial Sequence
<220> FEATURE:
<223> OTHER INFORMATION: primer

<400> SEQUENCE: 26
ttgggagcaa gagtggagtt                                                      20

<210> SEQ ID NO 27
<211> LENGTH: 22
<212> TYPE: PRT
<213> ORGANISM: Artificial Sequence
<220> FEATURE:
<223> OTHER INFORMATION: synthetic flg22 peptide

<400> SEQUENCE: 27

Gln Arg Leu Ser Thr Gly Ser Arg Ile Asn Ser Ala Lys Asp Asp Ala
1               5                   10                  15

Ala Gly Leu Gln Ile Ala
            20

<210> SEQ ID NO 28
<211> LENGTH: 18
<212> TYPE: PRT
<213> ORGANISM: Artificial Sequence
<220> FEATURE:
<223> OTHER INFORMATION: synthetic elf18

<400> SEQUENCE: 28

Ser Lys Glu Lys Phe Glu Arg Thr Lys Pro His Val Asn Val Gly Thr
1               5                   10                  15

Ile Gly

<210> SEQ ID NO 29
<211> LENGTH: 6
<212> TYPE: PRT
<213> ORGANISM: Artificial Sequence
<220> FEATURE:
<223> OTHER INFORMATION: synthetic control peptide

<400> SEQUENCE: 29

Glu Gln Val Ser Ala Val
1               5

<210> SEQ ID NO 30
<211> LENGTH: 1173
<212> TYPE: PRT
<213> ORGANISM: Arabidopsis thaliana

<400> SEQUENCE: 30

Met Lys Leu Leu Ser Lys Thr Phe Leu Ile Leu Thr Leu Thr Phe Phe
1               5                   10                  15

Phe Phe Gly Ile Ala Leu Ala Lys Gln Ser Phe Glu Pro Glu Ile Glu
                20                  25                  30

Ala Leu Lys Ser Phe Lys Asn Gly Ile Ser Asn Asp Pro Leu Gly Val
            35                  40                  45

Leu Ser Asp Trp Thr Ile Ile Gly Ser Leu Arg His Cys Asn Trp Thr
        50                  55                  60

Gly Ile Thr Cys Asp Ser Thr Gly His Val Val Ser Val Ser Leu Leu
65                  70                  75                  80

Glu Lys Gln Leu Glu Gly Val Leu Ser Pro Ala Ile Ala Asn Leu Thr
                85                  90                  95

Tyr Leu Gln Val Leu Asp Leu Thr Ser Asn Ser Phe Thr Gly Lys Ile
```

```
            100             105             110
Pro Ala Glu Ile Gly Lys Leu Thr Glu Leu Asn Gln Leu Ile Leu Tyr
        115                 120                 125
Leu Asn Tyr Phe Ser Gly Ser Ile Pro Ser Gly Ile Trp Glu Leu Lys
130                 135                 140
Asn Ile Phe Tyr Leu Asp Leu Arg Asn Asn Leu Leu Ser Gly Asp Val
145                 150                 155                 160
Pro Glu Glu Ile Cys Lys Thr Ser Ser Leu Val Leu Ile Gly Phe Asp
                165                 170                 175
Tyr Asn Asn Leu Thr Gly Lys Ile Pro Glu Cys Leu Gly Asp Leu Val
                180                 185                 190
His Leu Gln Met Phe Val Ala Ala Gly Asn His Leu Thr Gly Ser Ile
                195                 200                 205
Pro Val Ser Ile Gly Thr Leu Ala Asn Leu Thr Asp Leu Asp Leu Ser
        210                 215                 220
Gly Asn Gln Leu Thr Gly Lys Ile Pro Arg Asp Phe Gly Asn Leu Leu
225                 230                 235                 240
Asn Leu Gln Ser Leu Val Leu Thr Glu Asn Leu Leu Glu Gly Asp Ile
                245                 250                 255
Pro Ala Glu Ile Gly Asn Cys Ser Ser Leu Val Gln Leu Glu Leu Tyr
                260                 265                 270
Asp Asn Gln Leu Thr Gly Lys Ile Pro Ala Glu Leu Gly Asn Leu Val
                275                 280                 285
Gln Leu Gln Ala Leu Arg Ile Tyr Lys Asn Lys Leu Thr Ser Ser Ile
        290                 295                 300
Pro Ser Ser Leu Phe Arg Leu Thr Gln Leu Thr His Leu Gly Leu Ser
305                 310                 315                 320
Glu Asn His Leu Val Gly Pro Ile Ser Glu Ile Gly Phe Leu Glu
                325                 330                 335
Ser Leu Glu Val Leu Thr Leu His Ser Asn Asn Phe Thr Gly Glu Phe
                340                 345                 350
Pro Gln Ser Ile Thr Asn Leu Arg Asn Leu Thr Val Leu Thr Val Gly
                355                 360                 365
Phe Asn Asn Ile Ser Gly Glu Leu Pro Ala Asp Leu Gly Leu Leu Thr
370                 375                 380
Asn Leu Arg Asn Leu Ser Ala His Asp Asn Leu Leu Thr Gly Pro Ile
385                 390                 395                 400
Pro Ser Ser Ile Ser Asn Cys Thr Gly Leu Lys Leu Leu Asp Leu Ser
                405                 410                 415
His Asn Gln Met Thr Gly Glu Ile Pro Arg Gly Phe Gly Arg Met Asn
                420                 425                 430
Leu Thr Phe Ile Ser Ile Gly Arg Asn His Phe Thr Gly Glu Ile Pro
                435                 440                 445
Asp Asp Ile Phe Asn Cys Ser Asn Leu Glu Thr Leu Ser Val Ala Asp
        450                 455                 460
Asn Asn Leu Thr Gly Thr Leu Lys Pro Leu Ile Gly Lys Leu Gln Lys
465                 470                 475                 480
Leu Arg Ile Leu Gln Val Ser Tyr Asn Ser Leu Thr Gly Pro Ile Pro
                485                 490                 495
Arg Glu Ile Gly Asn Leu Lys Asp Leu Asn Ile Leu Tyr Leu His Ser
                500                 505                 510
Asn Gly Phe Thr Gly Arg Ile Pro Arg Glu Met Ser Asn Leu Thr Leu
                515                 520                 525
```

```
Leu Gln Gly Leu Arg Met Tyr Ser Asn Asp Leu Gly Pro Ile Pro
            530                 535                 540
Glu Glu Met Phe Asp Met Lys Leu Leu Ser Val Leu Asp Leu Ser Asn
545                 550                 555                 560
Asn Lys Phe Ser Gly Gln Ile Pro Ala Leu Phe Ser Lys Leu Glu Ser
                565                 570                 575
Leu Thr Tyr Leu Ser Leu Gln Gly Asn Lys Phe Asn Gly Ser Ile Pro
            580                 585                 590
Ala Ser Leu Lys Ser Leu Ser Leu Leu Asn Thr Phe Asp Ile Ser Asp
            595                 600                 605
Asn Leu Leu Thr Gly Thr Ile Pro Gly Glu Leu Leu Ala Ser Leu Lys
610                 615                 620
Asn Met Gln Leu Tyr Leu Asn Phe Ser Asn Asn Leu Leu Thr Gly Thr
625                 630                 635                 640
Ile Pro Lys Glu Leu Gly Lys Leu Glu Met Val Gln Glu Ile Asp Leu
                645                 650                 655
Ser Asn Asn Leu Phe Ser Gly Ser Ile Pro Arg Ser Leu Gln Ala Cys
                660                 665                 670
Lys Asn Val Phe Thr Leu Asp Phe Ser Gln Asn Asn Leu Ser Gly His
            675                 680                 685
Ile Pro Asp Glu Val Phe Gln Gly Met Asp Met Ile Ile Ser Leu Asn
            690                 695                 700
Leu Ser Arg Asn Ser Phe Ser Gly Glu Ile Pro Gln Ser Phe Gly Asn
705                 710                 715                 720
Met Thr His Leu Val Ser Leu Asp Leu Ser Asn Asn Leu Thr Gly
                725                 730                 735
Glu Ile Pro Glu Ser Leu Ala Asn Leu Ser Thr Leu Lys His Leu Lys
                740                 745                 750
Leu Ala Ser Asn Asn Leu Lys Gly His Val Pro Glu Ser Gly Val Phe
            755                 760                 765
Lys Asn Ile Asn Ala Ser Asp Leu Met Gly Asn Thr Asp Leu Cys Gly
770                 775                 780
Ser Lys Lys Pro Leu Lys Pro Cys Thr Ile Lys Gln Lys Ser Ser His
785                 790                 795                 800
Phe Ser Lys Arg Thr Arg Val Ile Leu Ile Ile Leu Gly Ser Ala Ala
                805                 810                 815
Ala Leu Leu Leu Val Leu Leu Leu Val Leu Ile Leu Thr Cys Cys Lys
            820                 825                 830
Lys Lys Glu Lys Lys Ile Glu Asn Ser Ser Glu Ser Ser Leu Pro Asp
            835                 840                 845
Leu Asp Ser Ala Leu Lys Leu Lys Arg Phe Glu Pro Lys Glu Leu Glu
850                 855                 860
Gln Ala Thr Asp Ser Phe Asn Ser Ala Asn Ile Ile Gly Ser Ser Ser
865                 870                 875                 880
Leu Ser Thr Val Tyr Lys Gly Gln Leu Glu Asp Gly Thr Val Ile Ala
                885                 890                 895
Val Lys Val Leu Asn Leu Lys Glu Phe Ser Ala Glu Ser Asp Lys Trp
                900                 905                 910
Phe Tyr Thr Glu Ala Lys Thr Leu Ser Gln Leu Lys His Arg Asn Leu
            915                 920                 925
Val Lys Ile Leu Gly Phe Ala Trp Glu Ser Gly Lys Thr Lys Ala Leu
930                 935                 940
```

Val Leu Pro Phe Met Glu Asn Gly Asn Leu Glu Asp Thr Ile His Gly
945                 950                 955                 960

Ser Ala Ala Pro Ile Gly Ser Leu Leu Glu Lys Ile Asp Leu Cys Val
                965                 970                 975

His Ile Ala Ser Gly Ile Asp Tyr Leu His Ser Gly Tyr Gly Phe Pro
                980                 985                 990

Ile Val His Cys Asp Leu Lys Pro Ala Asn Ile Leu Leu Asp Ser Asp
        995                 1000                1005

Arg Val Ala His Val Ser Asp Phe Gly Thr Ala Arg Ile Leu Gly
    1010                1015                1020

Phe Arg Glu Asp Gly Ser Thr Thr Ala Ser Thr Ser Ala Phe Glu
    1025                1030                1035

Gly Thr Ile Gly Tyr Leu Ala Pro Glu Phe Ala Tyr Met Arg Lys
    1040                1045                1050

Val Thr Thr Lys Ala Asp Val Phe Ser Phe Gly Ile Ile Met Met
    1055                1060                1065

Glu Leu Met Thr Lys Gln Arg Pro Thr Ser Leu Asn Asp Glu Asp
    1070                1075                1080

Ser Gln Asp Met Thr Leu Arg Gln Leu Val Glu Lys Ser Ile Gly
    1085                1090                1095

Asn Gly Arg Lys Gly Met Val Arg Val Leu Asp Met Glu Leu Gly
    1100                1105                1110

Asp Ser Ile Val Ser Leu Lys Gln Glu Glu Ala Ile Glu Asp Phe
    1115                1120                1125

Leu Lys Leu Cys Leu Phe Cys Thr Ser Ser Arg Pro Glu Asp Arg
    1130                1135                1140

Pro Asp Met Asn Glu Ile Leu Thr His Leu Met Lys Leu Arg Gly
    1145                1150                1155

Lys Ala Asn Ser Phe Arg Glu Asp Arg Asn Glu Asp Arg Glu Val
    1160                1165                1170

<210> SEQ ID NO 31
<211> LENGTH: 1031
<212> TYPE: PRT
<213> ORGANISM: Arabidopsis thaliana

<400> SEQUENCE: 31

Met Lys Leu Ser Phe Ser Leu Val Phe Asn Ala Leu Thr Leu Leu Leu
1               5                   10                  15

Gln Val Cys Ile Phe Ala Gln Ala Arg Phe Ser Asn Glu Thr Asp Met
            20                  25                  30

Gln Ala Leu Leu Glu Phe Lys Ser Gln Val Ser Glu Asn Asn Lys Arg
        35                  40                  45

Glu Val Leu Ala Ser Trp Asn His Ser Ser Pro Phe Cys Asn Trp Ile
    50                  55                  60

Gly Val Thr Cys Gly Arg Arg Glu Arg Val Ile Ser Leu Asn Leu
65                  70                  75                  80

Gly Gly Phe Lys Leu Thr Gly Val Ile Ser Pro Ser Ile Gly Asn Leu
                85                  90                  95

Ser Phe Leu Arg Leu Leu Asn Leu Ala Asp Asn Ser Phe Gly Ser Thr
            100                 105                 110

Ile Pro Gln Lys Val Gly Arg Leu Phe Arg Leu Gln Tyr Leu Asn Met
        115                 120                 125

Ser Tyr Asn Leu Leu Glu Gly Arg Ile Pro Ser Ser Leu Ser Asn Cys
    130                 135                 140

```
Ser Arg Leu Ser Thr Val Asp Leu Ser Ser Asn His Leu Gly His Gly
145                 150                 155                 160

Val Pro Ser Glu Leu Gly Ser Leu Ser Lys Leu Ala Ile Leu Asp Leu
            165                 170                 175

Ser Lys Asn Asn Leu Thr Gly Asn Phe Pro Ala Ser Leu Gly Asn Leu
        180                 185                 190

Thr Ser Leu Gln Lys Leu Asp Phe Ala Tyr Asn Gln Met Arg Gly Glu
    195                 200                 205

Ile Pro Asp Glu Val Ala Arg Leu Thr Gln Met Val Phe Phe Gln Ile
210                 215                 220

Ala Leu Asn Ser Phe Ser Gly Gly Phe Pro Pro Ala Leu Tyr Asn Ile
225                 230                 235                 240

Ser Ser Leu Glu Ser Leu Ser Leu Ala Asp Asn Ser Phe Ser Gly Asn
                245                 250                 255

Leu Arg Ala Asp Phe Gly Tyr Leu Leu Pro Asn Leu Arg Arg Leu Leu
            260                 265                 270

Leu Gly Thr Asn Gln Phe Thr Gly Ala Ile Pro Lys Thr Leu Ala Asn
        275                 280                 285

Ile Ser Ser Leu Glu Arg Phe Asp Ile Ser Ser Asn Tyr Leu Ser Gly
290                 295                 300

Ser Ile Pro Leu Ser Phe Gly Lys Leu Arg Asn Leu Trp Trp Leu Gly
305                 310                 315                 320

Ile Arg Asn Asn Ser Leu Gly Asn Asn Ser Ser Ser Gly Leu Glu Phe
                325                 330                 335

Ile Gly Ala Val Ala Asn Cys Thr Gln Leu Glu Tyr Leu Asp Val Gly
            340                 345                 350

Tyr Asn Arg Leu Gly Gly Glu Leu Pro Ala Ser Ile Ala Asn Leu Ser
        355                 360                 365

Thr Thr Leu Thr Ser Leu Phe Leu Gly Gln Asn Leu Ile Ser Gly Thr
370                 375                 380

Ile Pro His Asp Ile Gly Asn Leu Val Ser Leu Gln Glu Leu Ser Leu
385                 390                 395                 400

Glu Thr Asn Met Leu Ser Gly Glu Leu Pro Val Ser Phe Gly Lys Leu
                405                 410                 415

Leu Asn Leu Gln Val Val Asp Leu Tyr Ser Asn Ala Ile Ser Gly Glu
            420                 425                 430

Ile Pro Ser Tyr Phe Gly Asn Met Thr Arg Leu Gln Lys Leu His Leu
        435                 440                 445

Asn Ser Asn Ser Phe His Gly Arg Ile Pro Gln Ser Leu Gly Arg Cys
450                 455                 460

Arg Tyr Leu Leu Asp Leu Trp Met Asp Thr Asn Arg Leu Asn Gly Thr
465                 470                 475                 480

Ile Pro Gln Glu Ile Leu Gln Ile Pro Ser Leu Ala Tyr Ile Asp Leu
                485                 490                 495

Ser Asn Asn Phe Leu Thr Gly His Phe Pro Glu Glu Val Gly Lys Leu
            500                 505                 510

Glu Leu Leu Val Gly Leu Gly Ala Ser Tyr Asn Lys Leu Ser Gly Lys
        515                 520                 525

Met Pro Gln Ala Ile Gly Gly Cys Leu Ser Met Glu Phe Leu Phe Met
530                 535                 540

Gln Gly Asn Ser Phe Asp Gly Ala Ile Pro Asp Ile Ser Arg Leu Val
545                 550                 555                 560
```

-continued

```
Ser Leu Lys Asn Val Asp Phe Ser Asn Asn Leu Ser Gly Arg Ile
            565             570             575
Pro Arg Tyr Leu Ala Ser Leu Pro Ser Leu Arg Asn Leu Asn Leu Ser
        580             585             590
Met Asn Lys Phe Glu Gly Arg Val Pro Thr Thr Gly Val Phe Arg Asn
        595             600             605
Ala Thr Ala Val Ser Val Phe Gly Asn Thr Asn Ile Cys Gly Gly Val
    610             615             620
Arg Glu Met Gln Leu Lys Pro Cys Ile Val Gln Ala Ser Pro Arg Lys
625             630             635             640
Arg Lys Pro Leu Ser Val Arg Lys Lys Val Ser Gly Ile Cys Ile
            645             650             655
Gly Ile Ala Ser Leu Leu Leu Ile Ile Ile Val Ala Ser Leu Cys Trp
            660             665             670
Phe Met Lys Arg Lys Lys Lys Asn Ala Ser Asp Gly Asn Pro Ser
            675             680             685
Asp Ser Thr Thr Leu Gly Met Phe His Glu Lys Val Ser Tyr Glu Glu
        690             695             700
Leu His Ser Ala Thr Ser Arg Phe Ser Ser Thr Asn Leu Ile Gly Ser
705             710             715             720
Gly Asn Phe Gly Asn Val Phe Lys Gly Leu Leu Gly Pro Glu Asn Lys
            725             730             735
Leu Val Ala Val Lys Val Leu Asn Leu Leu Lys His Gly Ala Thr Lys
            740             745             750
Ser Phe Met Ala Glu Cys Glu Thr Phe Lys Gly Ile Arg His Arg Asn
            755             760             765
Leu Val Lys Leu Ile Thr Val Cys Ser Ser Leu Asp Ser Glu Gly Asn
    770             775             780
Asp Phe Arg Ala Leu Val Tyr Glu Phe Met Pro Lys Gly Ser Leu Asp
785             790             795             800
Met Trp Leu Gln Leu Glu Asp Leu Glu Arg Val Asn Asp His Ser Arg
            805             810             815
Ser Leu Thr Pro Ala Glu Lys Leu Asn Ile Ala Ile Asp Val Ala Ser
        820             825             830
Ala Leu Glu Tyr Leu His Val His Cys His Asp Pro Val Ala His Cys
    835             840             845
Asp Ile Lys Pro Ser Asn Ile Leu Leu Asp Asp Leu Thr Ala His
    850             855             860
Val Ser Asp Phe Gly Leu Ala Gln Leu Leu Tyr Lys Tyr Asp Arg Glu
865             870             875             880
Ser Phe Leu Asn Gln Phe Ser Ser Ala Gly Val Arg Gly Thr Ile Gly
            885             890             895
Tyr Ala Ala Pro Glu Tyr Gly Met Gly Gly Gln Pro Ser Ile Gln Gly
            900             905             910
Asp Val Tyr Ser Phe Gly Ile Leu Leu Leu Glu Met Phe Ser Gly Lys
    915             920             925
Lys Pro Thr Asp Glu Ser Phe Ala Gly Asp Tyr Asn Leu His Ser Tyr
    930             935             940
Thr Lys Ser Ile Leu Ser Gly Cys Thr Ser Ser Gly Gly Ser Asn Ala
945             950             955             960
Ile Asp Glu Gly Leu Arg Leu Val Leu Gln Val Gly Ile Lys Cys Ser
            965             970             975
Glu Glu Tyr Pro Arg Asp Arg Met Arg Thr Asp Glu Ala Val Arg Glu
```

```
                    980                 985                 990
Leu Ile Ser Ile Arg Ser Lys Phe Phe Ser Ser Lys Thr Thr Ile Thr
                995                1000                1005

Glu Ser Pro Arg Asp Ala Pro Gln Ser Ser Pro Gln Glu Trp Met
           1010                1015                1020

Leu Asn Thr Asp Met His Thr Met
       1025                1030

<210> SEQ ID NO 32
<211> LENGTH: 735
<212> TYPE: PRT
<213> ORGANISM: Arabidopsis thaliana

<400> SEQUENCE: 32

Met Lys Val Gln Glu Gly Leu Phe Leu Val Ala Ile Phe Phe Ser Leu
1               5                  10                  15

Ala Cys Thr Gln Leu Val Lys Gly Gln His Gln Pro Gly Glu Asn Cys
            20                  25                  30

Gln Asn Lys Cys Gly Asn Ile Thr Ile Glu Tyr Pro Phe Gly Ile Ser
        35                  40                  45

Ser Gly Cys Tyr Tyr Pro Gly Asn Glu Ser Phe Ser Ile Thr Cys Lys
    50                  55                  60

Glu Asp Arg Pro His Val Leu Ser Asp Ile Glu Val Ala Asn Phe Asn
65                  70                  75                  80

His Ser Gly Gln Leu Gln Val Leu Leu Asn Arg Ser Ser Thr Cys Tyr
                85                  90                  95

Asp Glu Gln Gly Lys Lys Thr Glu Glu Asp Ser Ser Phe Thr Leu Glu
            100                 105                 110

Asn Leu Ser Leu Ser Ala Asn Asn Lys Leu Thr Ala Val Gly Cys Asn
        115                 120                 125

Ala Leu Ser Leu Leu Asp Thr Phe Gly Met Gln Asn Tyr Ser Thr Ala
    130                 135                 140

Cys Leu Ser Leu Cys Asp Ser Pro Glu Ala Asp Gly Glu Cys Asn
145                 150                 155                 160

Gly Arg Gly Cys Cys Arg Val Asp Val Ser Ala Pro Leu Asp Ser Tyr
                165                 170                 175

Thr Phe Glu Thr Thr Ser Gly Arg Ile Lys His Met Thr Ser Phe His
            180                 185                 190

Asp Phe Ser Pro Cys Thr Tyr Ala Phe Leu Val Glu Asp Asp Lys Phe
        195                 200                 205

Asn Phe Ser Ser Thr Glu Asp Leu Leu Asn Leu Arg Asn Val Met Arg
    210                 215                 220

Phe Pro Val Leu Leu Asp Trp Ser Val Gly Asn Gln Thr Cys Glu Gln
225                 230                 235                 240

Val Gly Ser Thr Ser Ile Cys Gly Gly Asn Ser Thr Cys Leu Asp Ser
                245                 250                 255

Thr Pro Arg Asn Gly Tyr Ile Cys Arg Cys Asn Glu Gly Phe Asp Gly
            260                 265                 270

Asn Pro Tyr Leu Ser Ala Gly Cys Gln Asp Val Asn Glu Cys Thr Thr
        275                 280                 285

Ser Ser Thr Ile His Arg His Asn Cys Ser Asp Pro Lys Thr Cys Arg
    290                 295                 300

Asn Lys Val Gly Gly Phe Tyr Cys Lys Cys Gln Ser Gly Tyr Arg Leu
305                 310                 315                 320
```

-continued

```
Asp Thr Thr Thr Met Ser Cys Lys Arg Lys Glu Phe Ala Trp Thr Thr
            325                 330                 335

Ile Leu Leu Val Thr Thr Ile Gly Phe Leu Val Ile Leu Leu Gly Val
        340                 345                 350

Ala Cys Ile Gln Gln Arg Met Lys His Leu Lys Asp Thr Lys Leu Arg
            355                 360                 365

Glu Gln Phe Phe Glu Gln Asn Gly Gly Met Leu Thr Gln Arg Leu
370                 375                 380

Ser Gly Ala Gly Pro Ser Asn Val Asp Val Lys Ile Phe Thr Glu Asp
385                 390                 395                 400

Gly Met Lys Lys Ala Thr Asn Gly Tyr Ala Glu Ser Arg Ile Leu Gly
                405                 410                 415

Gln Gly Gly Gln Gly Thr Val Tyr Lys Gly Ile Leu Pro Asp Asn Ser
            420                 425                 430

Ile Val Ala Ile Lys Lys Ala Arg Leu Gly Asp Ser Ser Gln Val Glu
        435                 440                 445

Gln Phe Ile Asn Glu Val Leu Val Leu Ser Gln Ile Asn His Arg Asn
    450                 455                 460

Val Val Lys Leu Leu Gly Cys Cys Leu Glu Thr Glu Val Pro Leu Leu
465                 470                 475                 480

Val Tyr Glu Phe Ile Thr Asn Gly Thr Leu Phe Asp His Leu His Gly
                485                 490                 495

Ser Met Ile Asp Ser Ser Leu Thr Trp Glu His Arg Leu Lys Ile Ala
            500                 505                 510

Ile Glu Val Ala Gly Thr Leu Ala Tyr Leu His Ser Ser Ala Ser Ile
        515                 520                 525

Pro Ile Ile His Arg Asp Ile Lys Thr Ala Asn Ile Leu Leu Asp Val
    530                 535                 540

Asn Leu Thr Ala Lys Val Ala Asp Phe Gly Ala Ser Arg Leu Ile Pro
545                 550                 555                 560

Met Asp Lys Glu Glu Leu Glu Thr Met Val Gln Gly Thr Leu Gly Tyr
                565                 570                 575

Leu Asp Pro Glu Tyr Tyr Asn Thr Gly Leu Leu Asn Glu Lys Ser Asp
            580                 585                 590

Val Tyr Ser Phe Gly Val Val Leu Met Glu Leu Leu Ser Gly Gln Lys
        595                 600                 605

Ala Leu Cys Phe Lys Arg Pro Gln Ser Ser Lys His Leu Val Ser Tyr
    610                 615                 620

Phe Ala Thr Ala Thr Lys Glu Asn Arg Leu Asp Glu Ile Ile Gly Gly
625                 630                 635                 640

Glu Val Met Asn Glu Asp Asn Leu Lys Glu Ile Gln Glu Ala Ala Arg
                645                 650                 655

Ile Ala Ala Glu Cys Thr Arg Leu Met Gly Glu Glu Arg Pro Arg Met
            660                 665                 670

Lys Glu Val Ala Ala Lys Leu Glu Ala Leu Arg Val Glu Lys Thr Lys
        675                 680                 685

His Lys Trp Ser Asp Gln Tyr Pro Glu Glu Asn Glu His Leu Ile Gly
    690                 695                 700

Gly His Ile Leu Ser Ala Gln Gly Glu Thr Ser Ser Ile Gly Tyr
705                 710                 715                 720

Asp Ser Ile Lys Asn Val Ala Ile Leu Asp Ile Glu Thr Gly Arg
                725                 730                 735
```

```
<210> SEQ ID NO 33
<211> LENGTH: 25
<212> TYPE: PRT
<213> ORGANISM: Arabidopsis thaliana

<400> SEQUENCE: 33

Val Val Ser Gly Ile Cys Ile Gly Ile Ala Ser Leu Leu Ile Ile
1               5                   10                  15

Ile Val Ala Ser Leu Cys Trp Phe Met
            20                  25

<210> SEQ ID NO 34
<211> LENGTH: 25
<212> TYPE: PRT
<213> ORGANISM: Arabidopsis thaliana

<400> SEQUENCE: 34

Val Ile Leu Ile Ile Leu Gly Ser Ala Ala Leu Leu Val Leu
1               5                   10                  15

Leu Leu Val Leu Ile Leu Thr Cys Cys
            20                  25

<210> SEQ ID NO 35
<211> LENGTH: 25
<212> TYPE: PRT
<213> ORGANISM: Arabidopsis thaliana

<400> SEQUENCE: 35

Gly Ala Ile Ala Gly Gly Val Ala Ala Gly Ala Ala Leu Leu Phe Ala
1               5                   10                  15

Val Pro Ala Ile Ala Leu Ala Trp Trp
            20                  25

<210> SEQ ID NO 36
<211> LENGTH: 25
<212> TYPE: PRT
<213> ORGANISM: Homo sapiens

<400> SEQUENCE: 36

Ile Pro Ser Ile Ala Thr Gly Met Val Gly Ala Leu Leu Leu Leu Leu
1               5                   10                  15

Val Val Ala Leu Gly Ile Gly Leu Phe
            20                  25

<210> SEQ ID NO 37
<211> LENGTH: 365
<212> TYPE: PRT
<213> ORGANISM: Arabidopsis thaliana

<400> SEQUENCE: 37

Phe Phe Glu Gln Asn Gly Gly Met Leu Thr Gln Arg Leu Ser Gly
1               5                   10                  15

Ala Gly Pro Ser Asn Val Asp Val Lys Ile Phe Thr Glu Asp Gly Met
                20                  25                  30

Lys Lys Ala Thr Asn Gly Tyr Ala Glu Ser Arg Ile Leu Gly Gln Gly
            35                  40                  45

Gly Gln Gly Thr Val Tyr Lys Gly Ile Leu Pro Asp Asn Ser Ile Val
        50                  55                  60

Ala Ile Lys Lys Ala Arg Leu Gly Asp Ser Ser Gln Val Glu Gln Phe
65                  70                  75                  80

Ile Asn Glu Val Leu Val Leu Ser Gln Ile Asn His Arg Asn Val Val
```

85                  90                  95
Lys Leu Leu Gly Cys Cys Leu Glu Thr Glu Val Pro Leu Leu Val Tyr
            100                 105                 110

Glu Phe Ile Thr Asn Gly Thr Leu Phe Asp His Leu His Gly Ser Met
            115                 120                 125

Ile Asp Ser Ser Leu Thr Trp Glu His Arg Leu Lys Ile Ala Ile Glu
            130                 135                 140

Val Ala Gly Thr Leu Ala Tyr Leu His Ser Ser Ala Ser Ile Pro Ile
145                 150                 155                 160

Ile His Arg Asp Ile Lys Thr Ala Asn Ile Leu Leu Asp Val Asn Leu
                    165                 170                 175

Thr Ala Lys Val Ala Asp Phe Gly Ala Ser Arg Leu Ile Pro Met Asp
                180                 185                 190

Lys Glu Glu Leu Glu Thr Met Val Gln Gly Thr Leu Gly Tyr Leu Asp
            195                 200                 205

Pro Glu Tyr Tyr Asn Thr Gly Leu Leu Asn Glu Lys Ser Asp Val Tyr
            210                 215                 220

Ser Phe Gly Val Val Leu Met Glu Leu Leu Ser Gly Gln Lys Ala Leu
225                 230                 235                 240

Cys Phe Lys Arg Pro Gln Ser Ser Lys His Leu Val Ser Tyr Phe Ala
                245                 250                 255

Thr Ala Thr Lys Glu Asn Arg Leu Asp Glu Ile Ile Gly Gly Glu Val
                260                 265                 270

Met Asn Glu Asp Asn Leu Lys Glu Ile Gln Glu Ala Ala Arg Ile Ala
            275                 280                 285

Ala Glu Cys Thr Arg Leu Met Gly Glu Glu Arg Pro Arg Met Lys Glu
            290                 295                 300

Val Ala Ala Lys Leu Glu Ala Leu Arg Val Glu Lys Thr Lys His Lys
305                 310                 315                 320

Trp Ser Asp Gln Tyr Pro Glu Glu Asn Glu His Leu Ile Gly Gly His
                325                 330                 335

Ile Leu Ser Ala Gln Gly Glu Thr Ser Ser Ile Gly Tyr Asp Ser
                340                 345                 350

Ile Lys Asn Val Ala Ile Leu Asp Ile Glu Thr Gly Arg
            355                 360                 365

<210> SEQ ID NO 38
<211> LENGTH: 367
<212> TYPE: PRT
<213> ORGANISM: Arabidopsis thaliana

<400> SEQUENCE: 38

Phe Phe Glu Gln Asn Gly Gly Met Leu Ile Gln Arg Val Ser Gly
1               5                   10                  15

Ala Gly Pro Ser Asn Val Asp Val Lys Ile Phe Thr Glu Lys Gly Met
            20                  25                  30

Lys Glu Ala Thr Asn Gly Tyr His Glu Ser Arg Ile Leu Gly Gln Gly
            35                  40                  45

Gly Gln Gly Thr Val Tyr Lys Gly Ile Leu Pro Asp Asn Ser Ile Val
        50                  55                  60

Ala Ile Lys Lys Ala Arg Leu Gly Asn Arg Ser Gln Val Glu Gln Phe
65                  70                  75                  80

Ile Asn Glu Val Leu Val Leu Ser Gln Ile Asn His Arg Asn Val Val
                85                  90                  95

Lys Val Leu Gly Cys Cys Leu Glu Thr Glu Val Pro Leu Leu Val Tyr
                100                 105                 110

Glu Phe Ile Asn Ser Gly Thr Leu Phe Asp His Leu His Gly Ser Leu
            115                 120                 125

Tyr Asp Ser Ser Leu Thr Trp Glu His Arg Leu Arg Ile Ala Thr Glu
        130                 135                 140

Val Ala Gly Ser Leu Ala Tyr Leu His Ser Ser Ala Ser Ile Pro Ile
145                 150                 155                 160

Ile His Arg Asp Ile Lys Thr Ala Asn Ile Leu Leu Asp Lys Asn Leu
                165                 170                 175

Thr Ala Lys Val Ala Asp Phe Gly Ala Ser Arg Leu Ile Pro Met Asp
            180                 185                 190

Lys Glu Gln Leu Thr Thr Ile Val Gln Gly Thr Leu Gly Tyr Leu Asp
        195                 200                 205

Pro Glu Tyr Tyr Asn Thr Gly Leu Leu Asn Glu Lys Ser Asp Val Tyr
210                 215                 220

Ser Phe Gly Val Val Leu Met Glu Leu Leu Ser Gly Gln Lys Ala Leu
225                 230                 235                 240

Cys Phe Glu Arg Pro His Cys Pro Lys Asn Leu Val Ser Cys Phe Ala
                245                 250                 255

Ser Ala Thr Lys Asn Asn Arg Phe His Glu Ile Ile Asp Gly Gln Val
            260                 265                 270

Met Asn Glu Asp Asn Gln Arg Glu Ile Gln Glu Ala Ala Arg Ile Ala
        275                 280                 285

Ala Glu Cys Thr Arg Leu Met Gly Glu Glu Arg Pro Arg Met Lys Glu
290                 295                 300

Val Ala Ala Glu Leu Glu Ala Leu Arg Val Lys Thr Thr Lys Tyr Lys
305                 310                 315                 320

Trp Ser Asp Gln Tyr Arg Glu Thr Gly Glu Ile Glu His Leu Leu Gly
                325                 330                 335

Val Gln Ile Leu Ser Ala Gln Gly Glu Thr Ser Ser Ser Ile Gly Tyr
            340                 345                 350

Asp Ser Ile Arg Asn Val Thr Thr Leu Asp Ile Glu Ala Gly Arg
        355                 360                 365

<210> SEQ ID NO 39
<211> LENGTH: 365
<212> TYPE: PRT
<213> ORGANISM: Arabidopsis thaliana

<400> SEQUENCE: 39

Phe Phe Glu Gln Asn Gly Gly Met Leu Ile Gln Arg Leu Ser Gly
1               5                   10                  15

Ala Gly Leu Ser Asn Ile Asp Phe Lys Ile Phe Thr Glu Glu Gly Met
            20                  25                  30

Lys Glu Ala Thr Asn Gly Tyr Asp Glu Ser Arg Ile Leu Gly Gln Gly
        35                  40                  45

Gly Gln Gly Thr Val Tyr Lys Gly Ile Leu Pro Asp Asn Thr Ile Val
    50                  55                  60

Ala Ile Lys Lys Ala Arg Leu Ala Asp Ser Arg Gln Val Asp Gln Phe
65                  70                  75                  80

Ile His Glu Val Leu Val Leu Ser Gln Ile Asn His Arg Asn Val Val
                85                  90                  95

Lys Ile Leu Gly Cys Cys Leu Glu Thr Glu Val Pro Leu Leu Val Tyr
            100                 105                 110

Glu Phe Ile Thr Asn Gly Thr Leu Phe Asp His Leu His Gly Ser Ile
115                 120                 125

Phe Asp Ser Ser Leu Thr Trp Glu His Arg Leu Arg Ile Ala Ile Glu
130                 135                 140

Val Ala Gly Thr Leu Ala Tyr Leu His Ser Ala Ser Ile Pro Ile
145                 150                 155                 160

Ile His Arg Asp Ile Lys Thr Ala Asn Ile Leu Leu Asp Glu Asn Leu
                165                 170                 175

Thr Ala Lys Val Ala Asp Phe Gly Ala Ser Lys Leu Ile Pro Met Asp
            180                 185                 190

Lys Glu Gln Leu Thr Thr Met Val Gln Gly Thr Leu Gly Tyr Leu Asp
        195                 200                 205

Pro Glu Tyr Tyr Thr Thr Gly Leu Leu Asn Glu Lys Ser Asp Val Tyr
210                 215                 220

Ser Phe Gly Val Val Leu Met Glu Leu Leu Ser Gly Gln Lys Ala Leu
225                 230                 235                 240

Cys Phe Glu Arg Pro Gln Ala Ser Lys His Leu Val Ser Tyr Phe Val
                245                 250                 255

Ser Ala Thr Glu Glu Asn Arg Leu His Glu Ile Ile Asp Asp Gln Val
            260                 265                 270

Leu Asn Glu Asp Asn Leu Lys Glu Ile Gln Glu Ala Ala Arg Ile Ala
        275                 280                 285

Ala Glu Cys Thr Arg Leu Met Gly Glu Glu Arg Pro Arg Met Lys Glu
290                 295                 300

Val Ala Ala Lys Leu Glu Ala Leu Arg Val Glu Lys Thr Lys His Lys
305                 310                 315                 320

Trp Ser Asp Gln Tyr Pro Glu Glu Asn Glu His Leu Ile Gly Gly His
                325                 330                 335

Ile Leu Ser Ala Gln Gly Glu Thr Ser Ser Ile Gly Tyr Asp Ser
            340                 345                 350

Ile Lys Asn Val Ala Ile Leu Asp Ile Glu Thr Gly Arg
        355                 360                 365

<210> SEQ ID NO 40
<211> LENGTH: 367
<212> TYPE: PRT
<213> ORGANISM: Arabidopsis thaliana

<400> SEQUENCE: 40

Phe Phe Glu Gln Asn Gly Gly Met Leu Met Gln Arg Leu Ser Gly
1               5                   10                  15

Ala Gly Pro Ser Asn Val Asp Val Lys Ile Phe Thr Glu Glu Gly Met
            20                  25                  30

Lys Glu Ala Thr Asp Gly Tyr Asp Glu Asn Arg Ile Leu Gly Gln Gly
        35                  40                  45

Gly Gln Gly Thr Val Tyr Lys Gly Ile Leu Pro Asp Asn Ser Ile Val
    50                  55                  60

Ala Ile Lys Lys Ala Arg Leu Gly Asp Asn Ser Gln Val Glu Gln Phe
65                  70                  75                  80

Ile Asn Glu Val Leu Val Leu Ser Gln Ile Asn His Arg Asn Val Val
                85                  90                  95

Lys Leu Leu Gly Cys Cys Leu Glu Thr Glu Val Pro Leu Leu Val Tyr
            100                 105                 110

Glu Phe Ile Ser Ser Gly Thr Leu Phe Asp His Leu His Gly Ser Met

```
            115                 120                 125

Phe Asp Ser Ser Leu Thr Trp Glu His Arg Leu Arg Met Ala Val Glu
        130                 135                 140

Ile Ala Gly Thr Leu Ala Tyr Leu His Ser Ser Ala Ser Ile Pro Ile
145                 150                 155                 160

Ile His Arg Asp Ile Lys Thr Ala Asn Ile Leu Leu Asp Glu Asn Leu
                165                 170                 175

Thr Ala Lys Val Ala Asp Phe Gly Ala Ser Arg Leu Ile Pro Met Asp
            180                 185                 190

Lys Glu Asp Leu Ala Thr Met Val Gln Gly Thr Leu Gly Tyr Leu Asp
        195                 200                 205

Pro Glu Tyr Tyr Asn Thr Gly Leu Leu Asn Glu Lys Ser Asp Val Tyr
    210                 215                 220

Ser Phe Gly Val Val Leu Met Glu Leu Leu Ser Gly Gln Lys Ala Leu
225                 230                 235                 240

Cys Phe Glu Arg Pro Gln Thr Ser Lys His Ile Val Ser Tyr Phe Ala
                245                 250                 255

Ser Ala Thr Lys Glu Asn Arg Leu His Glu Ile Ile Asp Gly Gln Val
            260                 265                 270

Met Asn Glu Asn Asn Gln Arg Glu Ile Gln Lys Ala Ala Arg Ile Ala
        275                 280                 285

Val Glu Cys Thr Arg Leu Thr Gly Glu Glu Arg Pro Gly Met Lys Glu
    290                 295                 300

Val Ala Ala Glu Leu Glu Ala Leu Arg Val Thr Lys Thr Lys His Lys
305                 310                 315                 320

Trp Ser Asp Glu Tyr Pro Glu Gln Asp Thr Glu His Leu Val Gly
                325                 330                 335

Val Gln Lys Leu Ser Ala Gln Gly Glu Thr Ser Ser Ile Gly Tyr
            340                 345                 350

Asp Ser Ile Arg Asn Val Ala Ile Leu Asp Ile Glu Ala Gly Arg
        355                 360                 365

<210> SEQ ID NO 41
<211> LENGTH: 364
<212> TYPE: PRT
<213> ORGANISM: Arabidopsis thaliana

<400> SEQUENCE: 41

Phe Phe Glu Gln Asn Gly Gly Met Leu Ile Gln Arg Leu Ser Gly
1               5                   10                  15

Ala Gly Pro Ser Asn Val Asp Val Lys Ile Phe Thr Glu Glu Gly Met
            20                  25                  30

Lys Glu Ala Thr Asp Gly Tyr Asn Glu Ser Arg Ile Leu Gly Gln Gly
        35                  40                  45

Gly Gln Gly Thr Val Tyr Lys Gly Ile Leu Gln Asp Asn Ser Ile Val
    50                  55                  60

Ala Ile Lys Lys Ala Arg Leu Gly Asp Arg Ser Gln Val Glu Gln Phe
65                  70                  75                  80

Ile Asn Glu Val Leu Val Leu Ser Gln Ile Asn His Arg Asn Val Val
                85                  90                  95

Lys Leu Leu Gly Cys Cys Leu Glu Thr Glu Val Pro Leu Leu Val Tyr
            100                 105                 110

Glu Phe Ile Ser Ser Gly Thr Leu Phe Asp His Leu His Gly Ser Met
        115                 120                 125
```

```
Phe Asp Ser Ser Leu Thr Trp Glu His Arg Leu Arg Ile Ala Ile Glu
        130                 135                 140

Val Ala Gly Thr Leu Ala Tyr Leu His Ser Tyr Ala Ser Ile Pro Ile
145                 150                 155                 160

Ile His Arg Asp Val Lys Thr Ala Asn Ile Leu Leu Asp Glu Asn Leu
                165                 170                 175

Thr Ala Lys Val Ala Asp Phe Gly Ala Ser Arg Leu Ile Pro Met Asp
            180                 185                 190

Gln Glu Gln Leu Thr Thr Met Val Gln Gly Thr Leu Gly Tyr Leu Asp
        195                 200                 205

Pro Glu Tyr Tyr Asn Thr Gly Leu Leu Asn Lys Ser Asp Val Tyr
210                 215                 220

Ser Phe Gly Val Val Leu Met Glu Leu Leu Ser Gly Glu Lys Ala Leu
225                 230                 235                 240

Cys Phe Glu Arg Pro Gln Ser Ser Lys His Leu Val Ser Tyr Phe Val
                245                 250                 255

Ser Ala Met Lys Glu Asn Arg Leu His Glu Ile Ile Asp Gly Gln Val
            260                 265                 270

Met Asn Glu Tyr Asn Gln Arg Glu Ile Gln Glu Ser Ala Arg Ile Ala
        275                 280                 285

Val Glu Cys Thr Arg Ile Met Gly Glu Glu Arg Pro Ser Met Lys Glu
290                 295                 300

Val Ala Ala Glu Leu Glu Ala Leu Arg Val Lys Thr Thr Lys His Gln
305                 310                 315                 320

Trp Ser Asp Gln Tyr Pro Lys Glu Val Glu His Leu Leu Gly Val Gln
                325                 330                 335

Ile Leu Ser Thr Gln Gly Asp Thr Ser Ser Ile Gly Tyr Asp Ser Ile
            340                 345                 350

Gln Asn Val Thr Arg Leu Asp Ile Glu Thr Gly Arg
        355                 360

<210> SEQ ID NO 42
<211> LENGTH: 369
<212> TYPE: PRT
<213> ORGANISM: Arabidopsis thaliana

<400> SEQUENCE: 42

Phe Phe Lys Arg Asn Gly Gly Leu Leu Leu Lys Gln Gln Leu Thr Thr
1               5                   10                  15

Arg Gly Gly Asn Val Glu Ser Ser Lys Ile Phe Ser Ser Lys Glu Leu
            20                  25                  30

Glu Lys Ala Thr Asp Asn Phe Asn Met Asn Arg Val Leu Gly Gln Gly
        35                  40                  45

Gly Gln Gly Thr Val Tyr Lys Gly Met Leu Val Asp Gly Arg Ile Val
    50                  55                  60

Ala Val Lys Arg Ser Lys Val Leu Asp Glu Asp Lys Val Glu Glu Phe
65                  70                  75                  80

Ile Asn Glu Val Gly Val Leu Ser Gln Ile Asn His Arg Asn Ile Val
                85                  90                  95

Lys Leu Met Gly Cys Cys Leu Gln Thr Glu Val Pro Ile Leu Val Tyr
            100                 105                 110

Glu His Ile Pro Asn Gly Asp Leu Phe Lys Arg Leu His His Asp Ser
        115                 120                 125

Asp Asp Tyr Thr Met Thr Trp Asp Val Arg Leu Arg Ile Ala Val Glu
    130                 135                 140
```

```
Ile Ala Gly Ala Leu Ala Tyr Leu His Ser Ala Ala Ser Thr Pro Val
145                 150                 155                 160

Tyr His Arg Asp Val Lys Thr Thr Asn Ile Leu Leu Asp Glu Lys Tyr
                165                 170                 175

Arg Ala Lys Val Ser Asp Phe Gly Thr Ser Arg Ser Ile Asn Val Asp
            180                 185                 190

Gln Thr His Leu Thr Thr Leu Val Ala Gly Thr Phe Gly Tyr Leu Asp
        195                 200                 205

Pro Glu Tyr Phe Gln Thr Ser Gln Phe Thr Asp Lys Ser Asp Val Tyr
    210                 215                 220

Ser Phe Gly Val Val Leu Val Glu Leu Ile Thr Gly Glu Lys Pro Phe
225                 230                 235                 240

Ser Val Met Arg Pro Glu Glu Asn Arg Gly Leu Val Ser His Phe Asn
                245                 250                 255

Glu Ala Met Lys Gln Asn Arg Val Leu Asp Ile Val Asp Ser Arg Ile
            260                 265                 270

Lys Glu Gly Cys Thr Leu Glu Gln Val Leu Ala Val Ala Lys Leu Ala
        275                 280                 285

Arg Arg Cys Leu Ser Leu Lys Gly Lys Lys Arg Pro Asn Met Arg Glu
    290                 295                 300

Val Ser Ile Glu Leu Glu Arg Ile Arg Ser Ser Pro Glu Asp Leu Glu
305                 310                 315                 320

Leu His Ile Glu Glu Glu Asp Glu Glu Glu Cys Ala Met Glu Ile Asn
                325                 330                 335

Met Asp Asp Ser Trp Ser Val Asp Met Thr Ala Pro Ala Ser Leu Phe
            340                 345                 350

Asp Leu Ser Pro Lys Leu Asp Val Glu Pro Leu Val Pro Gln Arg Thr
        355                 360                 365

Trp
```

CONSTRUCTS EXPRESSING CHIMERIC RECEPTORS AND USE THEREOF FOR THE CONTROLLED ACTIVATION OF DEFENCE RESPONSE TO PATHOGENS IN PLANTS

CROSS-REFERENCE TO RELATED APPLICATIONS

This application is a 371 of PCT/EP2010/057845, filed on Jun. 4, 2010, which claims the benefit of Italian Patent Application No. RM2009A000279, filed Jun. 4, 2009, the contents of each of which are incorporated herein by reference.

FIELD OF THE INVENTION

The instant invention refers to the construction and use, in plants, of chimeric genes that allow controlled activation of defense responses to pathogens organisms. The invention finds application in the agro-industrial field.

BACKGROUND

The innate immunity, a defense system which is common to vertebrates and invertebrates, is based on the recognition of molecules of microbial origin, known as Pathogen-Associated Molecular Patterns or PAMPs (Pathogen-Associated Molecular Patterns) and molecules of endogenous origin, named HAMPs (Host-Associated Molecular Patterns) or DAMPs (Damage-Associated Molecular Patterns), which indicate the presence of potential pathogens.

In plants, an example of DAMPs is represented by oligogalacturonides (OG), molecules derived from the degradation of the pectic component of the wall, due to polygalacturonases released by pathogens micro-organisms during invasion.

OGs function as danger signals and induce the expression of defense genes and proteins (Ridley 2001, Denoux 2008, Casasoli 2008, Galletti 2008, Casasoli 2009), protecting plants against fungal diseases (Ferrari 2007). Besides inducing defense responses, OGs also affect several aspects of plant growth and development (Ridley, 2001, Bellincampi 1996). Both at the structural and the functional level, OGs are reminiscent of the hyaluronan fragments of the animal extracellular matrix, a well known class of DAMPs involved in wound response and healing (Jiang, 2007). Like that of hyaluronan fragments, biological activity of OGs is related to their molecular size, since fragments with a degree of polymerization (DP) comprised between 10 and 15 are the most active (13, 14).

Notably, the "egg box" conformation is necessary for the biological activity of OGs (Ridley, 2001, Cabrera 2008).

The more studied PAMPs are the bacterial flagellin and the elongation factor Tu (EF-Tu) that, in *Arabidopsis*, are perceived by two LRR receptor kinase (LRR-RLK, Leucine-Rich Repeat Receptor-Like Kinase), called FLS2 and EFR, respectively. These proteins are analogous to human TLR receptors (Toll-Like Receptor) and consist of an extracellular LRR domain, a single-stranded transmembrane region and an intracellular kinase domain of the serine/threonine type. The recognition of the ligand in the two systems, flagellin/FLS2 and EF-Tu/EFR, determines the activation of complex defense responses, largely shared, like the expression of genes involved in defense responses, the accumulation of ethylene, callose, hydrogen peroxide and finally the induction of hypersensitivity response. It is also known that the EFR receptor, after the recognition of its ligand, activates these defense responses not only in *Arabidopsis* but in other plant species, too (Lacombe, 2010).

There are many phytopathogens of different origin, such as viral, bacterial and fungal that can significantly reduce the productivity of crops, causing lesions in the plant tissues, reducing the development of leaves, roots or seeds. In absence of obvious symptoms, pathogens can cause a general metabolic disorder that reduces the productivity of the plants themselves. Pathogens can cause damage to pre- or post-harvest. Strategies for chemical control of diseases have obvious disadvantages, due to high costs and occasional toxicity for the non-target organisms.

Cell wall is the extracellular matrix that separates the plant cell from the external environment and plays a fundamental role in filtering and interpreting external cues such as pathogen attack, wounding or mechanical stress (Kohorn 2000; Brownlee 2002). Pectin, a component of the cell wall that is continually modified and remodelled during plant growth and development, is a complex polymer that determines the porosity, hydration and plasticity of the wall as well as cell-cell adhesion. Moreover, pectin is critical for physiological processes such as pollen growth (Stenzel et al., 2008) and compatibility (Lord 2003), root and stem elongation, seed germination and fruit ripening (Micheli 2001; Pilling et al., 2004) as well as for response to pathogens not just as a mechanical barrier but also as a sensor for incoming infections (Vorwerk et al., 2004); The characteristic of pectin that determines maintenance of the wall integrity and cohesion of the cells is due to the polyanionic nature of its backbone, i.e. homogalacturonan, which is capable of binding calcium to form the structures called "egg-box". These structures can occasionally be hydrolysed and fragmented by enzymes of microbial or vegetal origin, to release the OG which perform regulative and activation actions of defense responses (Cervone et al., 1989). Treatment of plant tissues with OGs causes accumulation of reactive oxygen species, biosynthesis of phytoalexins and expression of pathogenesis-related (PR) proteins (Ridley et al., 2001). In *Arabidopsis* OGs induce the expression of genes and defense proteins (Denoux et al., 2008; Casasoli et al., 2008) and protect the plant against fungal diseases (Ferrari et al., 2007). In analogy with the role of hyaluronan fragments in the animal innate immunity, OGs may be regarded as host-associated molecular patterns (HAMPS); (Taylor & Gallo 2006; Stern et al., 2006)). Besides inducing defense responses, OGs also affect several aspects of plant growth and development (Bellincampi et al., 1996; Mauro et al., 2002).

Since the response of *Arabidopsis* to OGs largely overlaps that to PAMPs flg22 (peptide derived from bacterial flagellin) (Denoux et al., 2008) and elft 8 (peptide derived from EF-Tu (Zipfel et al., 2006) it has been hypothesized that the receptor of OGs is similar to the receptors Flagellin Sensing 2 (FLS2) and Elongation Factor Tu Receptor (EFR). These are members of the leucine-rich repeat (LRR) receptor kinase (RK) family (Zipfel 2008; Sanabria et al., 2008) and the observation that an extracellular LRR protein, i.e. the polygalacturonase-inhibiting protein PGIP, interacts with OGs supports this hypothesis (Spadoni et al., 2006). On the other hand, candidate receptors of OGs are also some members of the Wall-Associated Kinase (WAK) family.

The WAK proteins are kinase-proteins belonging to the RLK (Receptor Like Kinase) family, showing an intracellular kinase domain of the Ser/Thr type and an extracellular domain containing multiple repeats, similar to epidermal growth factor (EGF) (He et al., 1996). In *Arabidopsis*, there are five genes that are tightly packed and highly correlated (WAK1-WAK5); they are expressed in leaves and meristems subjected to expansion, and are induced by pathogens, wounding and mechanical stress (He et al. 1996; Verica et al., 2003). The WAK family correlates with another family called WAK-like which includes 22 members (Verica & He 2002). WAK1 (At1g21250), the best characterized gene, is highly expressed in green organs and is induced by salicylic acid, and encodes a mature protein of 711 amino acids (He et al., 1998). WAK1 binds in vitro to the non-methyl esterificated homogalacturonan, to the OG with a degree of polymerization between 9 and 14 active as elicitor and compatible with the formation of "egg-box" structures calcium-induced (Decreux & Messiaen 2005, Cabrera et al., 2008). The antisense and inducible expression of WAK2 or WAK4 causes a reduction of WAK protein levels and a dwarf phenotype (Wagner & Kohorn 2001, Lally et al., 2001). The knock out mutant wak2 showed a dependence on sugar (and salt) for sprout's growth, suggesting that the WAK proteins are involved in the regulation of sugar metabolism (Kohorn et al., 2006b).

However, the precise role of individual WAK receptors remains largely unknown (Decreux & Messiaen 2005).

In *Arabidopsis, only a minimal number of the over* 600 RLKs have been characterized (Shiu et al., 2004; Afzal et al., 2008) and the possible occurrence within this superfamily of multiple members with similar and redundant function makes a reverse genetic approach (gene knock-out) for the identification of the receptors perceiving a pleiotropic signal like OGs, very difficult.

The construction of chimeric receptors, constituted by domains of different proteins, is an alternative approach for the biochemical and functional characterization of RLKs. Domain swaps have been widely used to study animal receptors (Tauszig et al., 2000; Tsujita et al., 2004; Weber et al., 2005), while in *Arabidopsis* it has been reported only one example in which the LRR ectodomain of the receptor kinase BRI1 is fused to the serine/threonine kinase domain of the rice gene product Xa21 and is able to initiate plant defense responses in rice cells upon treatment with brassinosteroids (He et al., 2000). Using a similar design, the ectodomain-TM-iJM portion of the rice resistance gene Xa3/Xa26 was fused to the kinase domains of either MRKa or MRKc, which belong to the same gene family as Xa3/Xa26 and expressed in rice. The transgenic plants were reported to be partially resistant to *Xanthomonas oryzae* pv. *oryzae* (Cao et al., 2007b).

DESCRIPTION OF THE INVENTION

The authors of the instant invention have developed a chimeric gene construct which exploits the peculiarities of two receptors, FLS2 and EFR, as well as of WAK receptors. The applicative purpose of the instant invention is the development and use of plants with an enhanced and controlled defense against pathogens. In a particular aspect, the chimeric construct is based on fusion of the FLS2 extracellular domain with the transmembrane (TM) and intracellular domain of EFR, potent activation domain of defense responses, or WAK. The authors expressed transiently and stably the chimeric gene FLS2-EFR under the control of the constitutive promoter CaMV 35S in *Arabidopsis* plants and in a Solanacea, *Nicotiana tabacum*. Transformed plants, upon treatment with flg22, internalize the receptor and activate marker genes of resistance response mediated by EFR such as accumulation of ethylene, hydrogen peroxide and activation of marker genes of the EFR-mediated responses. Therefore, it is possible to use the portion of the EFR receptor which includes TM and kinase domains in combination with the extracellular portion of FLS2 and/or of other plant receptors that respond to signalling molecules other than those which EFR responds to. The constructs of the invention are of the $ED_{R1}$-$TM_{R2}$-$ID_{R2}$ type, where R1 and R2 are two receptor kinases, TM is the transmembrane domain, and ED and ID are respectively the extracellular and intracellular domain. The use of such constructs allow to have a defense response which is controlled, targeted and enhanced, with the aim of increasing resistance to many different phytopatogenic organisms.

The authors of the instant invention have thus demonstrated that it is possible to design and use plant functional chimeric receptors in order to identify the function of a specific receptor by a chimeric approach. Upon defining the most appropriate design of the chimeras the authors have shown that EFR is amenable to the construction of functional chimeric receptors able to activate defense against pathogens. Finally, the authors obtained EFR-based chimeras, using the extracellular domain of WAK1 as a candidate receptor of OGs, demonstrating that WAK1 is able to sense OGs in vivo and to trigger a defense response.

The invention also refers to plants transformed with chimeric constructs of the invention. The constructs express molecules able to recognize a ligand of any kind, and to activate specifically and in a controlled manner the defense responses of the plants. This technology is applicable to all plants of agronomic interest. The use of plants with a controlled regulation of defense responses considerably reduces the use of pesticides.

It is an object of the present invention a construct able to express, in at least one plant tissue, a chimeric receptor, said chimeric receptor being composed essentially of:

a) the extracellular portion, comprising the external juxtamembrane portion, of a first kinase receptor R1;

b) the transmembrane portion and the intracellular portion, comprising the internal juxtamembrane portion of a second kinase receptor R2, wherein R1 and R2 are different. Preferably the first kinase receptor R1 is selected from the group: FLS2 receptor able to recognize bacterial flagellin, EFR receptor able to recognize the bacterial transcription elongation factor, receptor belonging to the WAK kinase family.

More preferably the receptors derived from *Arabidopsis thaliana*.

In the instant invention, for % of identity (or % of similarity) it is intended the quantification of the % of elements equal (or similar) in a sequence of a biomolecule. (Larkin et at., 2007).

In a preferred embodiment, the extracellular portion of the FLS2 receptor, or a part thereof, has essentially a sequence comprised between aa 1 and aa 806 of the sequence present in NCBI database with the No. NP 199445 (SEQ ID NO: 30) or has an amino acid sequence with a % identity not less than 70% of said FLS2 sequence.

In a more preferred embodiment, the extracellular portion of the EFR receptor or a part thereof has essentially a sequence comprised between aa 1 and aa 649 of the sequence present in NCBI database with the No. NP 197548.1 (SEQ ID NO: 31), or has an amino acid sequence with a % identity not less than 70% of said EFR sequence.

In a more preferred embodiment the extracellular portion of the WAK1 receptor or a part thereof has essentially a sequence comprised between aa 1 and aa 333 of the sequence present in NCBI database with the No. NP 564137.1 (SEQ ID NO: 32), or has an amino acid sequence with a % identity not less than 70% of said WAK1 sequence.

In a preferred embodiment the first kinase receptor R1 is a receptor able to recognize a ligand derived from phytopatogens, released or produced during the infection, as defined by Boller T. & Felix G., 2009.

In a still preferred embodiment the second kinase receptor R2 is selected from the group of: EFR receptor, receptor belonging to the family of WAK kinases.

Preferably the second kinase receptors derive from *Arabidopsis thaliana*.

In a preferred embodiment the intracellular portion of the EFR receptor has essentially the sequence from aa 650 to aa 1031 of the sequence present in NCBI database with the No. NP 197548.1 (SEQ ID NO: 31), or has an amino acid sequence with % identity not less than 70% of said EFR sequence.

In a further preferred embodiment the intracellular portion is that of the WAK1 receptor, and has essentially the sequence from aa 334 to aa 735 of the sequence present in NCBI database with the No. NP 564137.1 (SEQ ID NO: 32), or has an amino acid sequence with % indentity not less than 70% of said WAK1 sequence.

In a further preferred embodiment the transmembrane portion and the intracellular portion (also including the internal juxtamembrane portion) of EFR is fused with the extracellular portion of the FLS2 or WAK1 receptor, or of a receptor recognizing a ligand derived from phytopathogens, or released, or produced during the infection.

In a preferred embodiment the transmembrane portion and the intracellular portion (also including the internal juxtamembrane portion) of WAK1 is fused with the extracellular portion of the EFR receptor, or of a receptor recognizing a ligand derived from phytopathogens, released or produced during the infection.

It is an object of the invention, the use of the construct as described above, for the transformation of plants or plant tissues or plant cells, either transiently or stably It is an object of the invention plants transformed with the chimeric constructs of the invention or parts of the transformed plant.

Preferably the transformed plants are resistant to fungal and/or bacterial pathogens such as *B. cinerea, P. syringae* and/or *P. carotovorum*.

BRIEF DESCRIPTION OF THE DRAWINGS

The present invention will now be described in experimental non-exhaustive examples, with reference to the following figures.

A) The coding regions of EFR and FLS2 are labelled in white and grey, respectively, with the region corresponding to the signal peptide indicated in black. eJMC and iJM, external and internal juxtamembrane portion, respectively; TM, transmembrane region. All genes were fused to the GFP-encoding sequence and placed under the control of the CaMV 35S promoter. NOS: nos terminator. The junction points in the two chimeric receptors are indicated. YXXΦ and PEST sequences are respectively marked by (♦) and (★).

B) Amino acid sequence of the transmembrane domains of EFR (NP 197548.1; SEQ ID NO: 31), FLS2 (NP 199445; SEQ ID NO: 30) and BAKI (Q94F62). Regions matching a dimerization consensus sequence GXXXG identified in the epidermal growth factor receptor 1 (ErbBl: P00533) (Mendrola et al., 2002) are labelled in grey.

Figure 2:
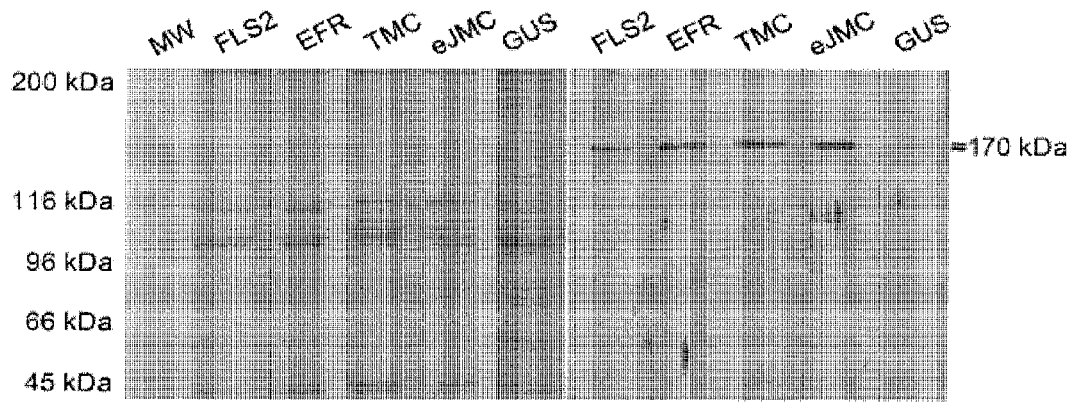
Figure 2:
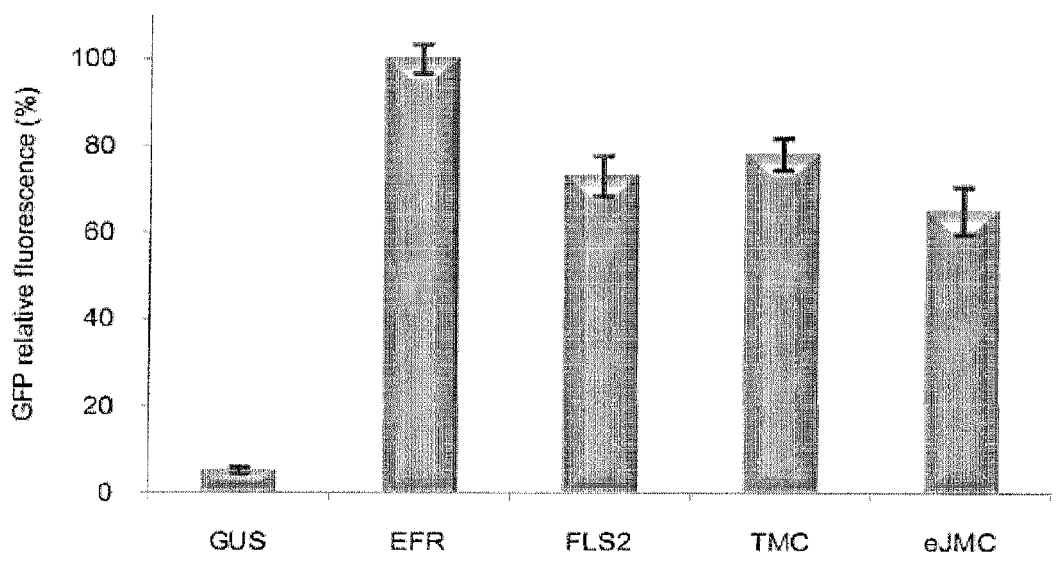
Figure 2:
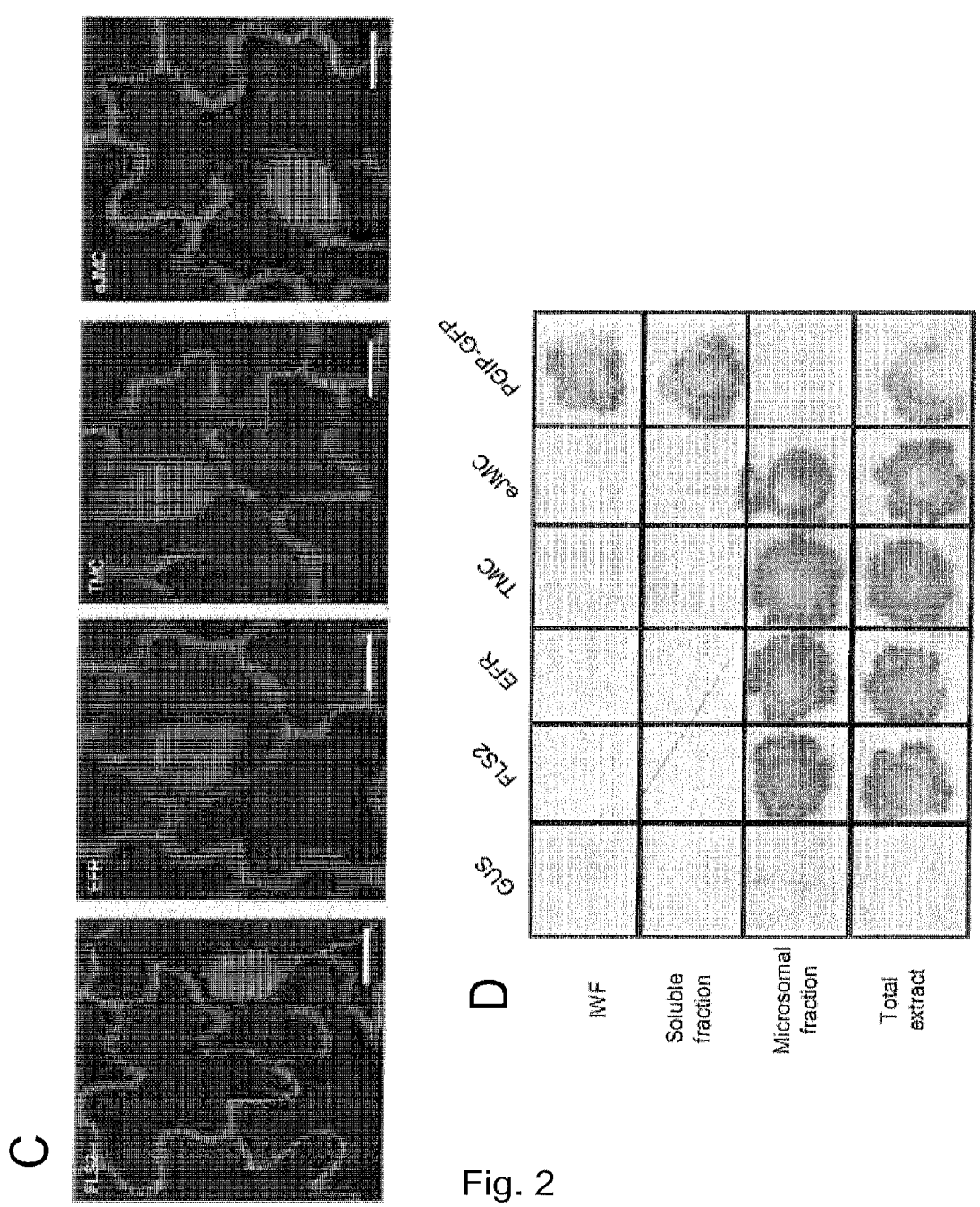

FIG. 2: Localization of FLS2, EFR, eJMC and TMC transiently expressed in *Arabidopsis thaliana* Col-0.

A) Western blot analysis using total protein extracts from agroinfiltrated *A. thaliana* Col-0 leaves expressing the indicated fluorescent protein fusions using GFP-specific antibodies (right panel). Coomassie staining is shown (left panel). *Agrobacterium* carrying pBI-GUS was used as a positive control for infection and a negative control for western blot analysis.

B) GFP relative fluorescence level in agroinfiltrated *Arabidopsis* leaves expressing the indicated protein fusions. Results are averages±standard error (n=3).

C) Analysis of receptor expression revealed by confocal fluorescence microscopy of *Arabidopsis* agroinfiltrated leaves. Figures show single cross-sections of leaf epidermal cells showing localization of fluorescent FLS2, EFR, eJMC or TMC in correspondence of the plasma membrane. For all samples, bars correspond to 10 μm.

D) Dot blot analysis using GFP-specific antibodies of proteins of microsomal fractions or intercellular washing fluids (IWF) obtained from agroinfiltrated *Arabidopsis* leaves expressing the indicated protein fusions. Agroinfiltrated leaves expressing a PvPGIP2-GFP protein fusion were used as a control for expression of an apoplastic protein (De Lorenzo & Ferrari 2002).

Figure 3:
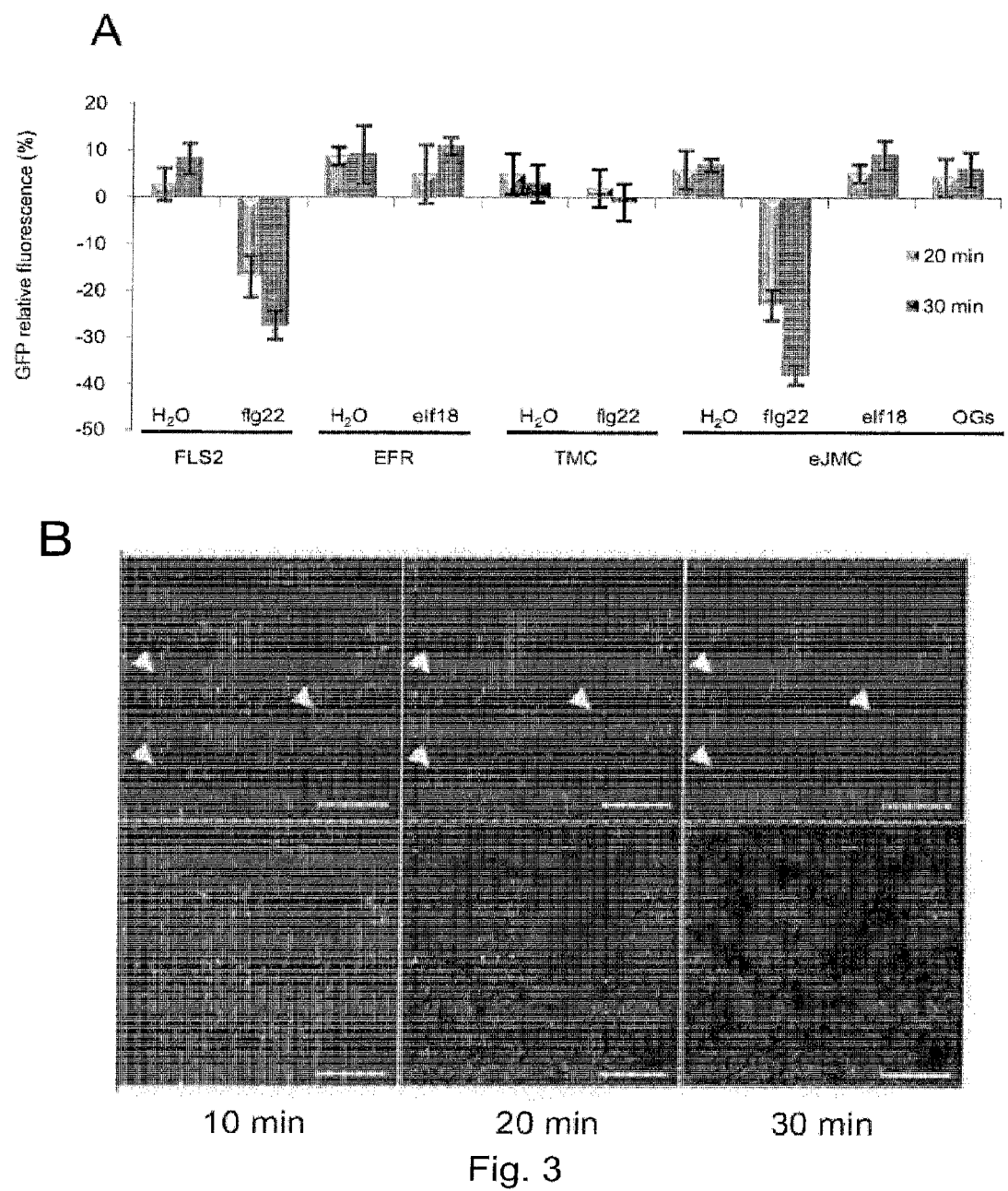
Figure 3:
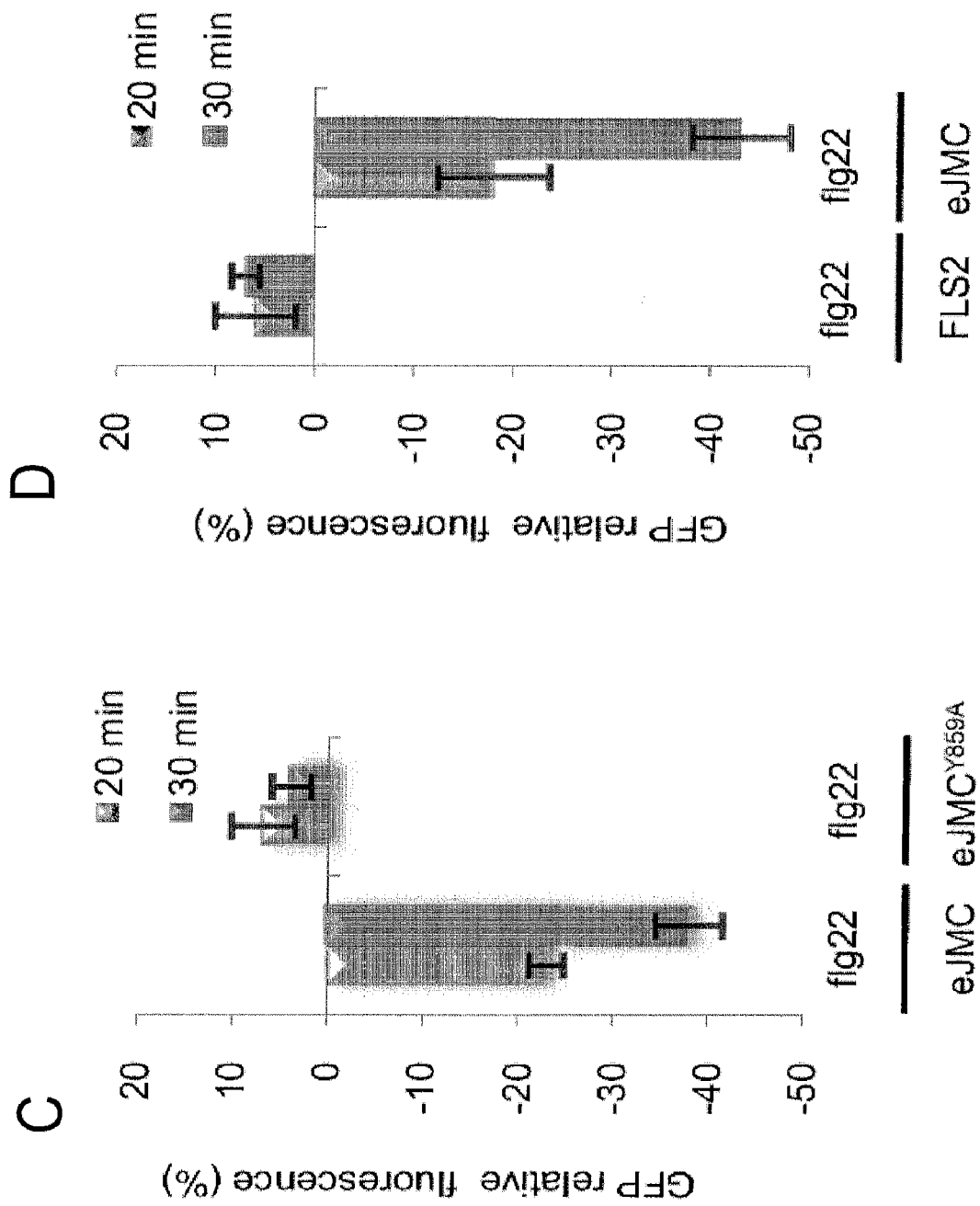
Figure 3:
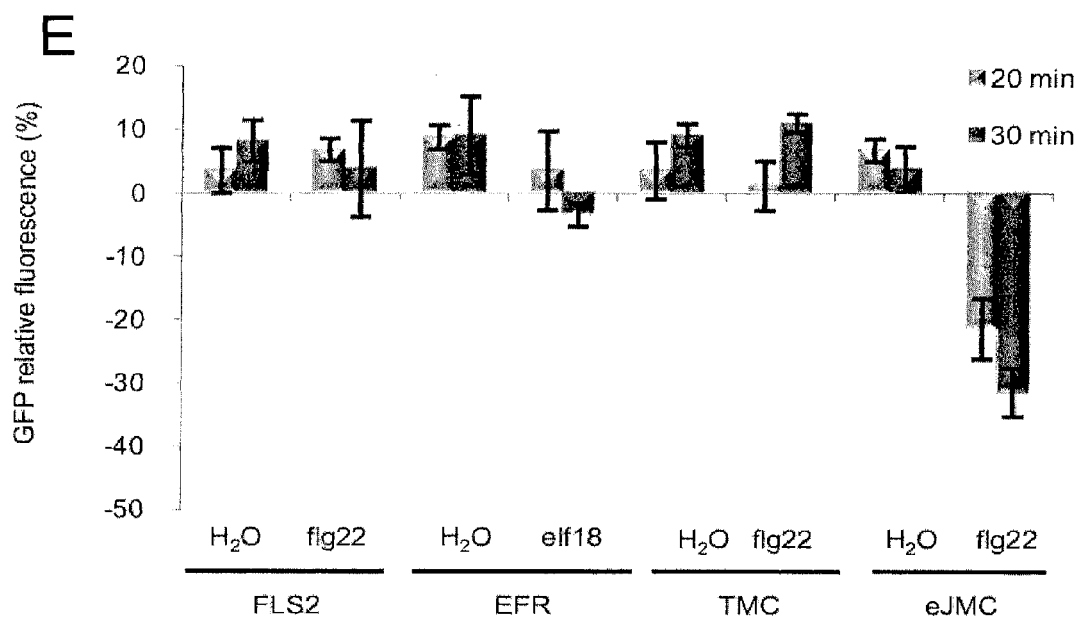
Figure 3:
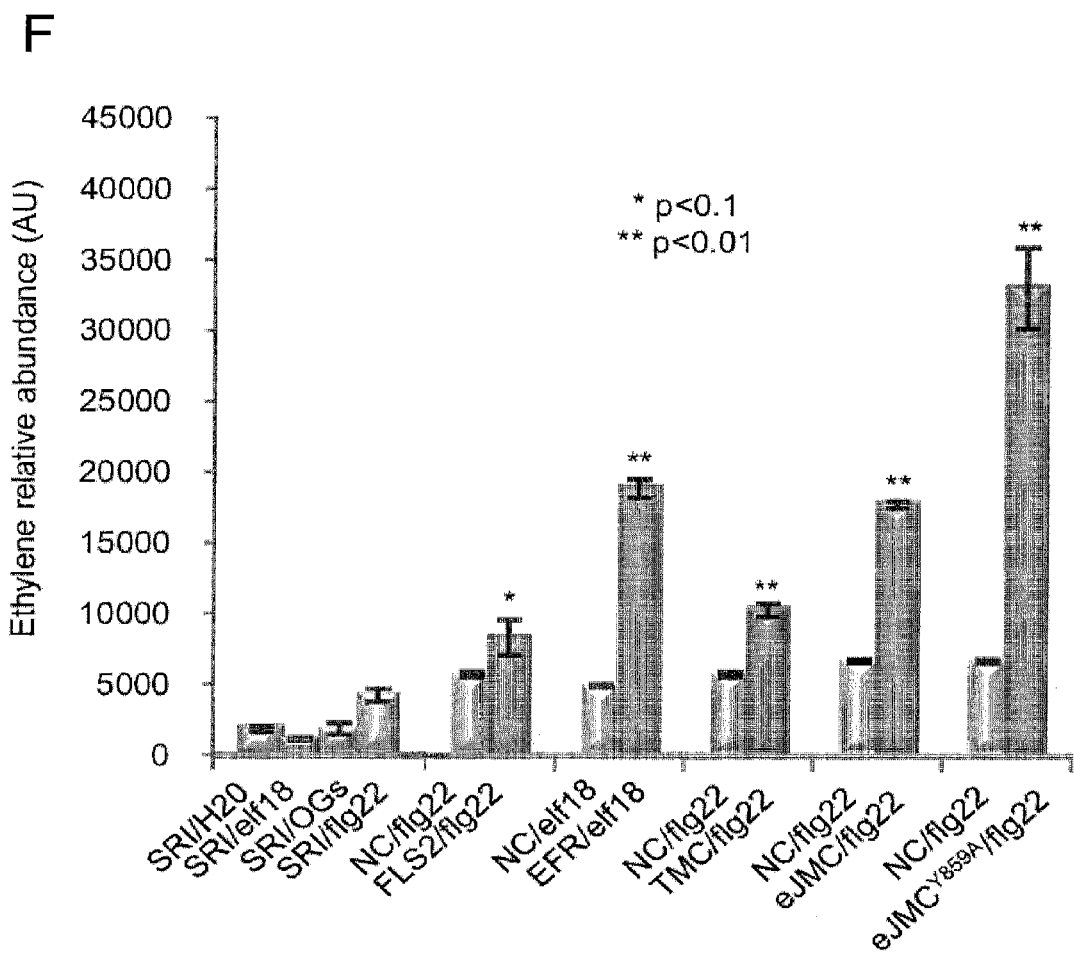
Figures 1, 3:
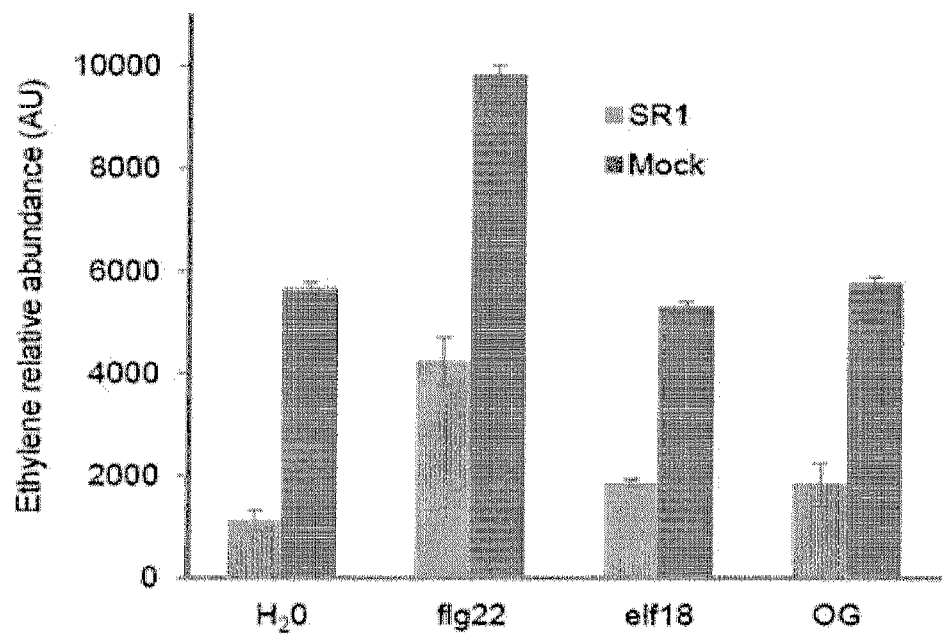

FIG. 3: Characterization of transiently expressed chimeric receptors

A) Relative variation of fluorescence in agroinfiltrated *Arabidopsis* leaves expressing the indicated receptors. Infiltrated sectors were excised, washed and treated for 30 min with 10 μM flg22 or elfl8 or 100 μg/ml OGs. Each value was normalised against fluorescence measured after 10 min of stimulation. Error bars indicate the standard error of three independent replicates.

B) Fluorescence micrographs of merged cross-sections (375 μm×375 μm×20 μm) during a treatment with 10 μM flg22 for 30 min of agroinfiltrated *Arabidopsis* leaf sectors expressing eJMC. Arrows indicate areas of the tissue showing the decreasing fluorescence signal.

C) Relative variation of fluorescence in agroinfiltrated *Arabidopsis* leaves expressing eJMC and eJMC$^{Y859A}$, and treated for 30 min with 10 μM flg22. Each value was normalised against fluorescence measured after 10 min of stimulation.

D) Relative variation of fluorescence in agroinfiltrated leaves of the *Arabidopsis* bak1-4 mutant expressing the indicated receptors and treated for 30 min with 10 μM flg22. Each value was normalised against fluorescence measured after 10 min of stimulation.

E) Relative variation of fluorescence in agroinfiltrated tobacco leaves expressing EFR, FLS2, eJMC and TMC and treated with 10 μM elfl8 or 10 μM flg22 for 30 min.

F) Induction of ethylene biosynthesis in agroinfiltrated tobacco leaves expressing the fluorescent EFR, FLS2, TMC, eJMC and eJMC$^{Y859A}$. Excised infiltrated leaf sectors were stimulated for 2 h with the elicitor (10 μM) as indicated in the figure. NC: negative control, represented by agroinfiltrated leaf tissues expressing fluorescent EFR or FLS2 and elicited with flg22 or elfl8, respectively. Results are averages±standard error (n=3).

Figure 1:
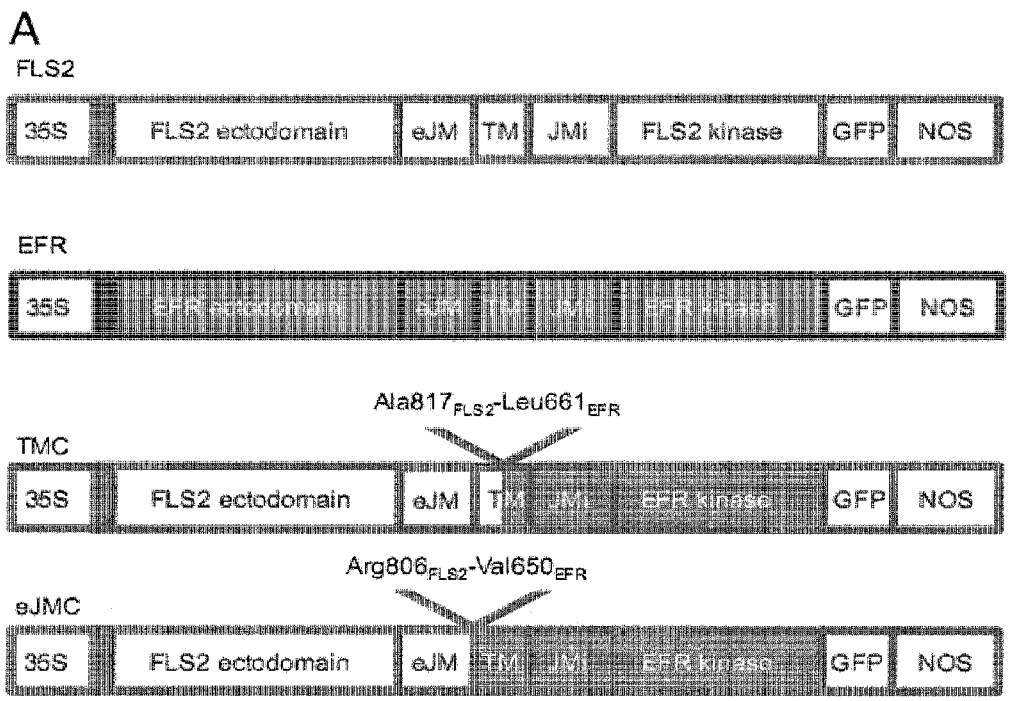
FIG. 1: Constructs for the expression of the FLS2/EFR chimeric receptors.

FIG. 3-1: Induction of ethylene biosynthesis in non-agroinfiltrated tobacco leaves (SR1) and in leaves infiltrated with *Agrobacterium* carrying the empty vector (mock).

Excised infiltrated leaf sectors were stimulated for 2 h with water or the elicitor (10 μM for flg22, 1 μM for elfl8 and 100 μg/ml for OGs). Values are means±s.e.m. (N=3).

Figure 4:
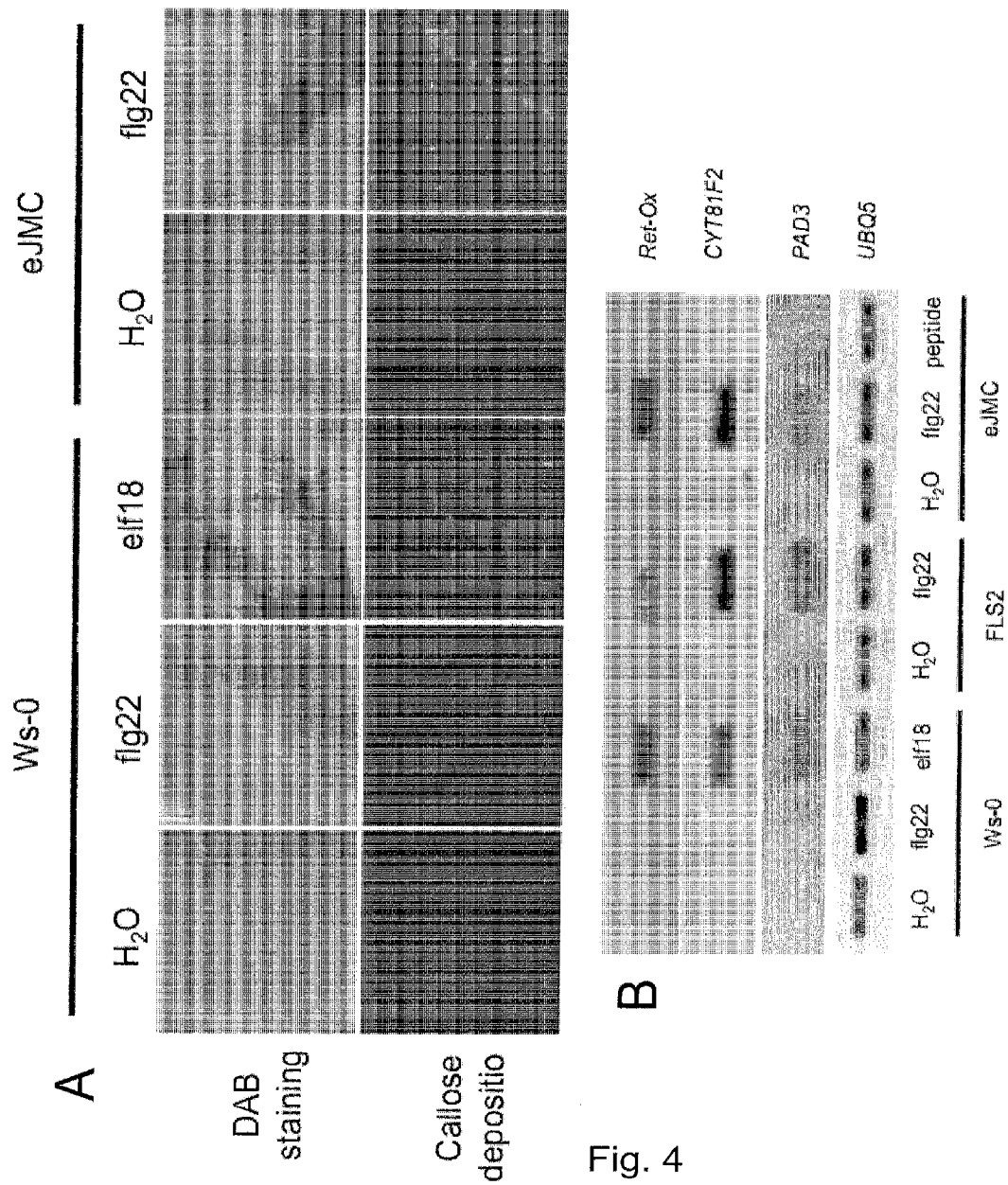
Figure 4:
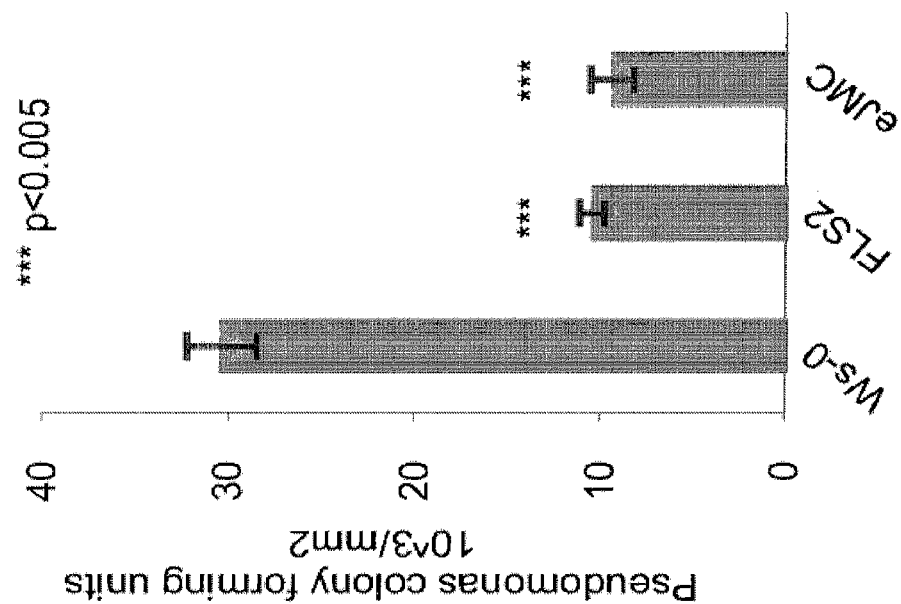
Figure 4:
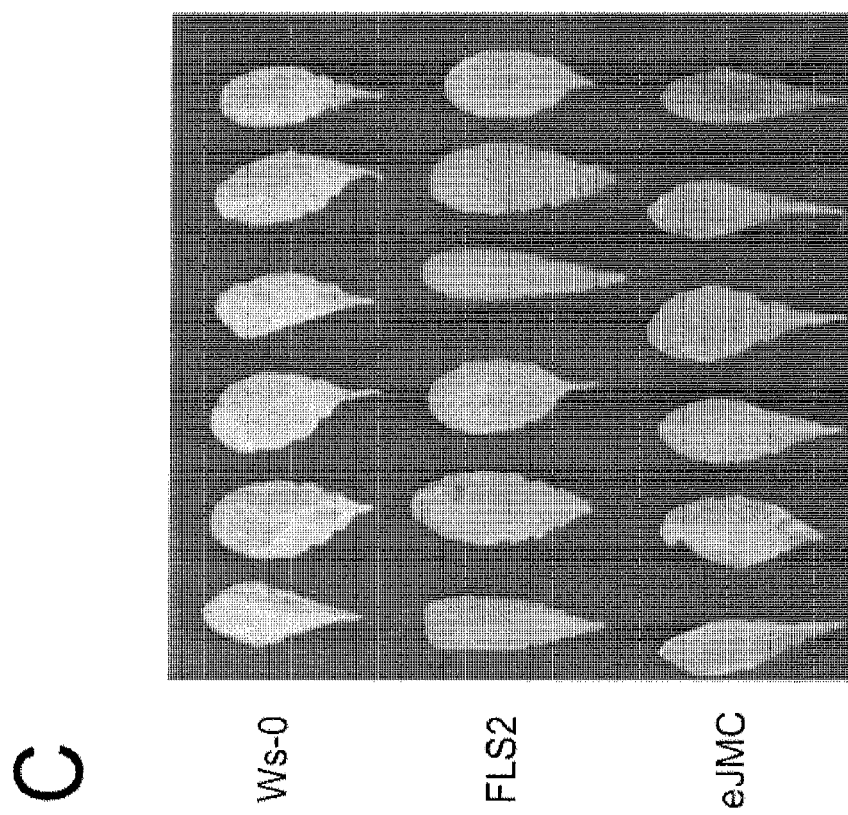

FIG. 4: Expression of eJMC restore flg22 sensing system in Ws-0 stably transformed.

A) Histochemical analysis of defense responses upon 1 h of treatment with $H_2O$, flg22 (1 µM) or elf18 (10 µM). Upper panel shows $H_2O_2$ accumulation revealed by DAB staining. Lower panel show callose deposition revealed by aniline blue staining.

B) Elicitor induced accumulation of Ret-Ox, CYP81F2 and PAD3 transcripts analysed by semi-quantitative PCR, using the UBQ5 gene for normalization. Leaves were incubated with water, flg22 (1 µM), elf18 (10 µM) or a generic peptide (10 µM) for 30 minutes. The experiment was repeated three times with similar results. The same experiment was performed in a second independent transgenic line expressing eJMC with similar results.

C) *Pseudomonas* DC3000 infections. (Left Panel) Symptoms disease of wild type and transformed plants after 4 days post infection. (Right panel) Growth of *Pseudomonas syringae* DC3000 after 4 day post infection. ***, $p<0.005$.

Figure 5:
Figure 5:
Figure 5:
Figure 5:
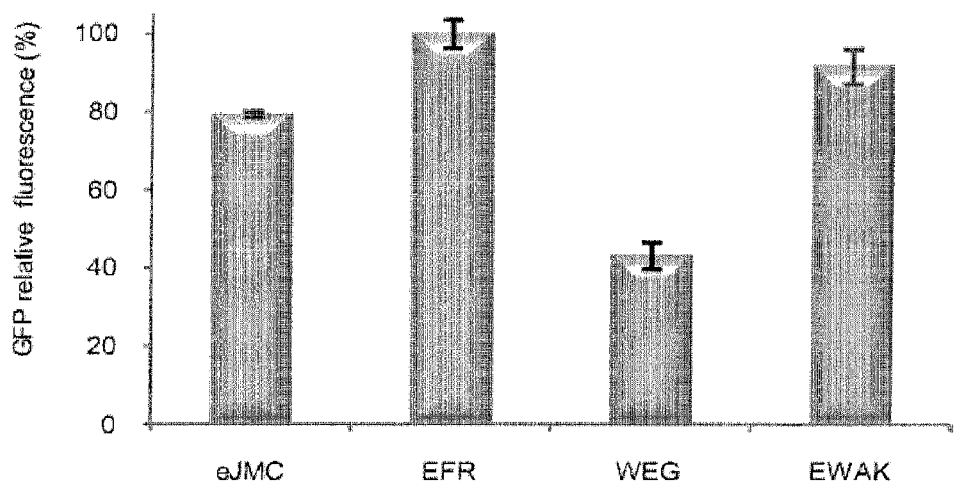
Figure 5:
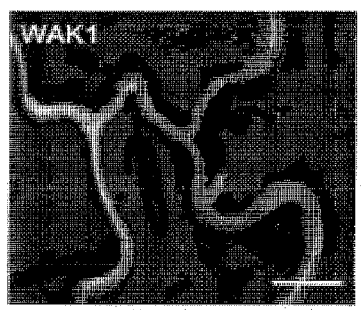
Figure 5:
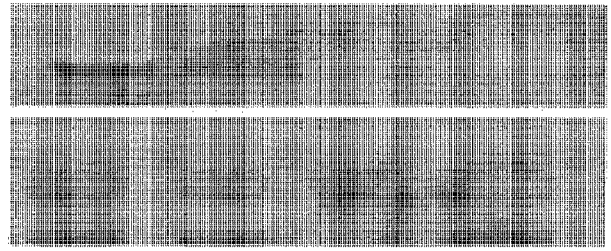
Figure 5:
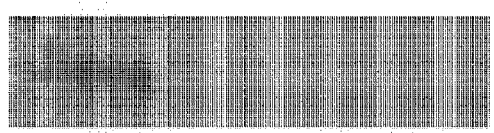

FIG. 5: Constructs for the expression of WAK1/EFR chimeric receptors.

A) The coding regions of EFR and WAK1 are labelled in white and dark grey, respectively, with the region corresponding to the signal peptides indicated in black. All genes were fused to the GFP-encoding sequence and placed under the control of the CaMV 35S promoter. NOS: nos terminator Annotated amino acids indicate the junction points in the two chimeric receptors. The YXXΦ sequence is marked by (♦).

B) Relative fluorescence level in agroinfiltrated *Arabidopsis* Col-0 leaves expressing the indicated fluorescent protein fusions (at 2 dpi). Results are averages±standard error (n=3).

C) Analysis of receptor expression revealed by confocal fluorescence microscopy of *Arabidopsis* agroinfiltrated leaves. Micrographs show single cross-sections of leaf epidermal cells and localization of fluorescent WAK1, WEG or EWAK in correspondence of the plasma membrane. For all samples, bars correspond to 10 µm.

D) Western blot analysis using GFP-specific antibodies (upper panel) of proteins of microsomal fractions or IWF obtained from agroinfiltrated *Arabidopsis* leaves expressing the indicated protein fusions and Coomassie staining shown for equal loading (lower panel). eJMC was used as positive control, while a non-fluorescent version of the WEG chimera (WE) was used as a negative control.

Figure 6:
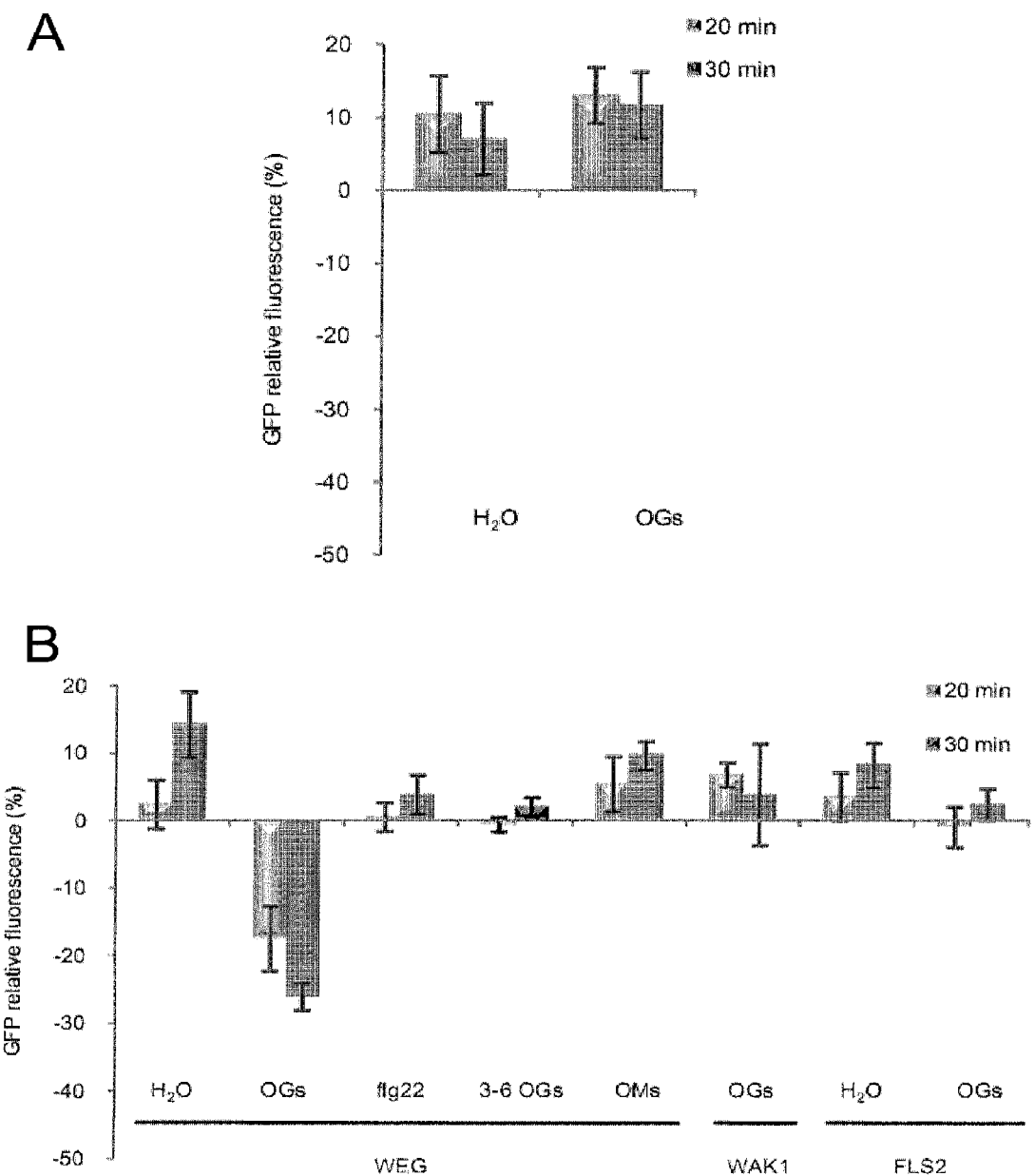
Figure 6:
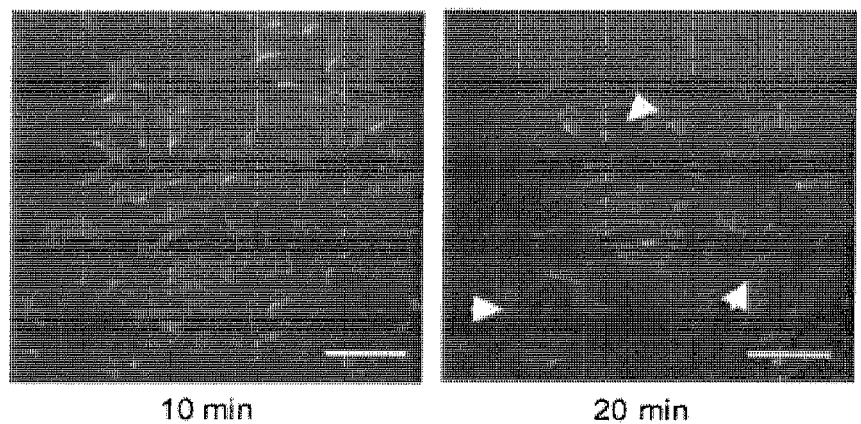
Figure 6:
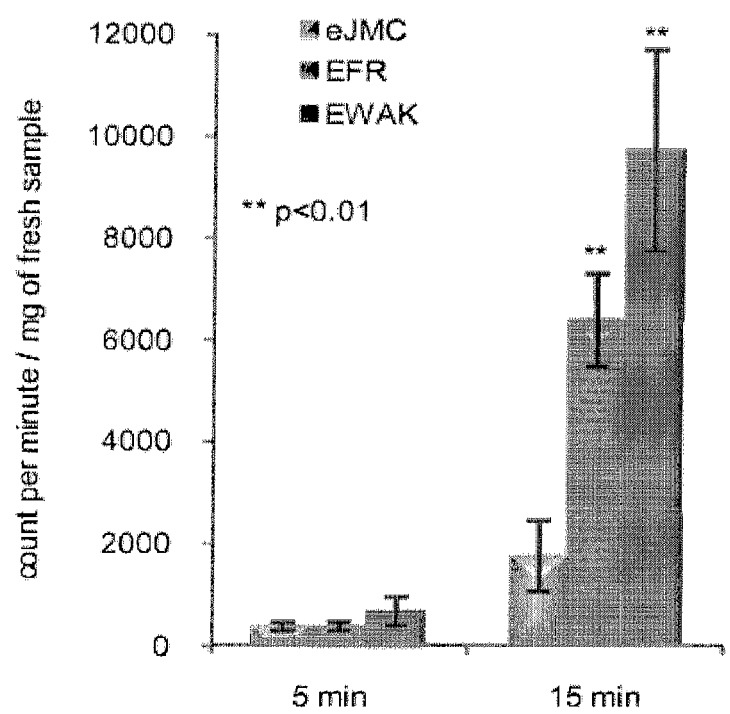
Figure 6:
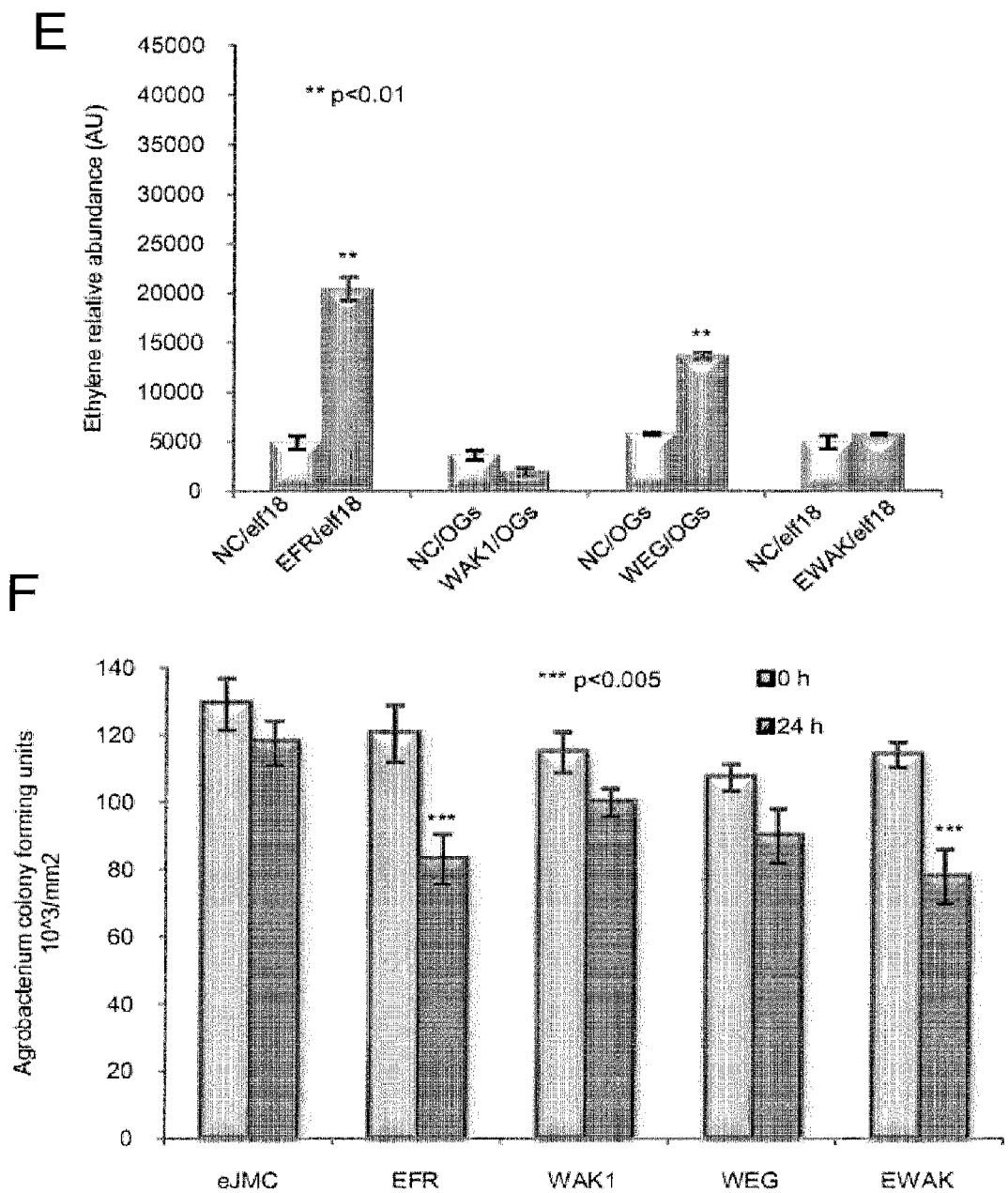
Figures 1, 6:
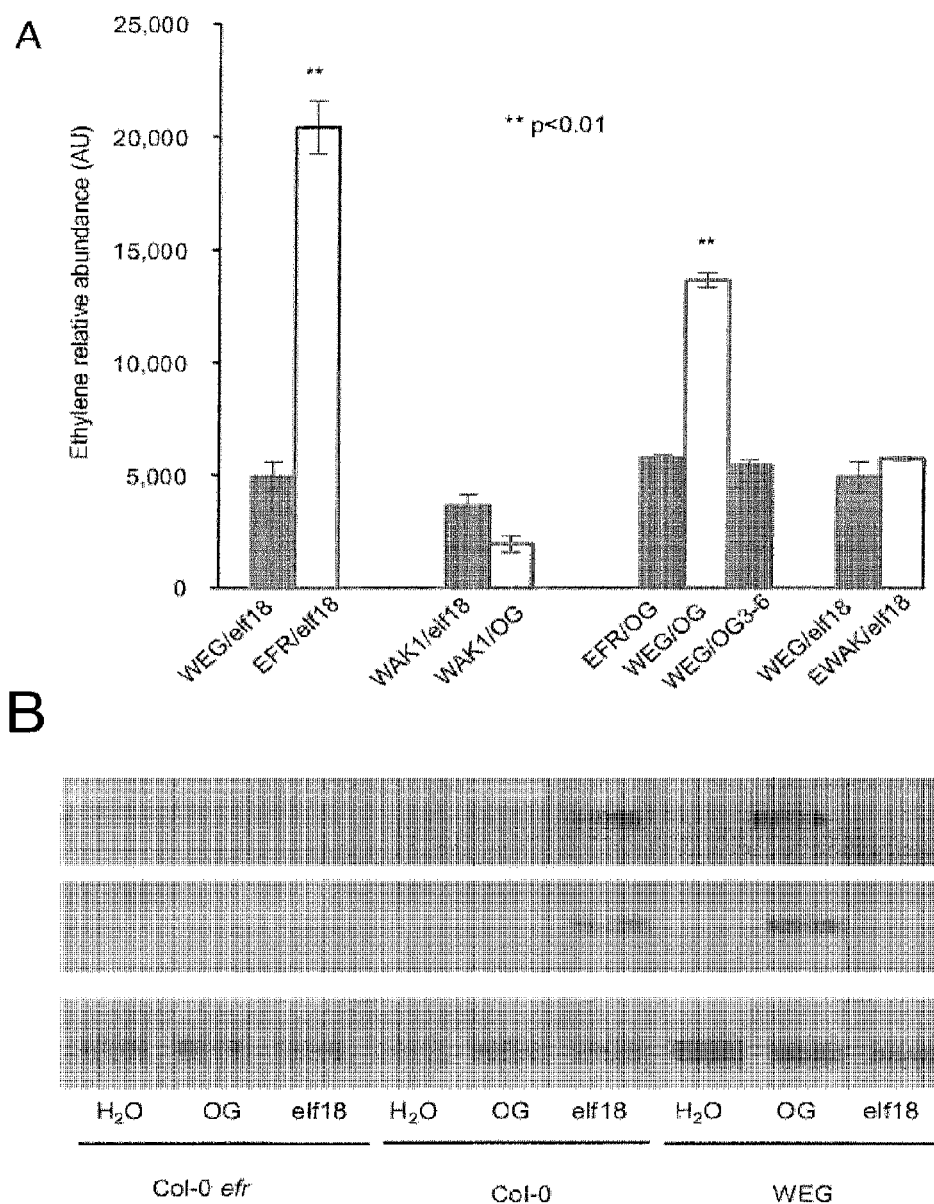
Figures 1, 6:
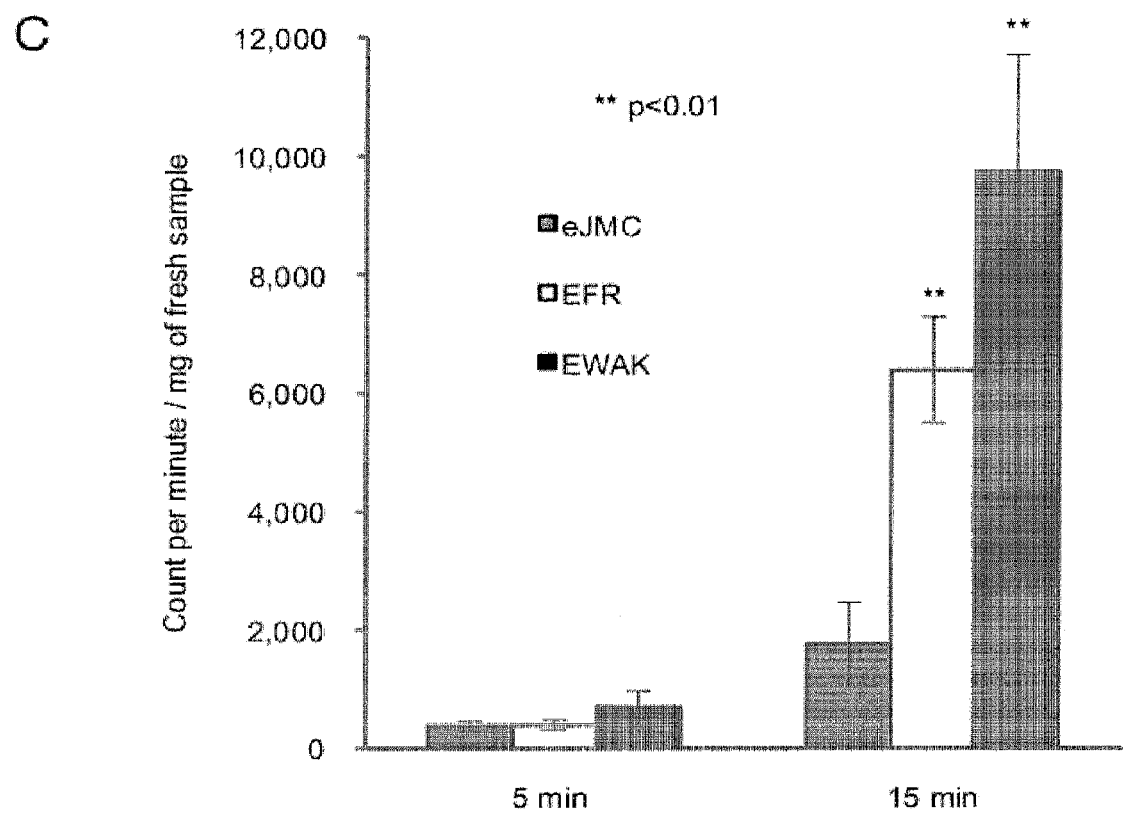
Figures 2, 6:
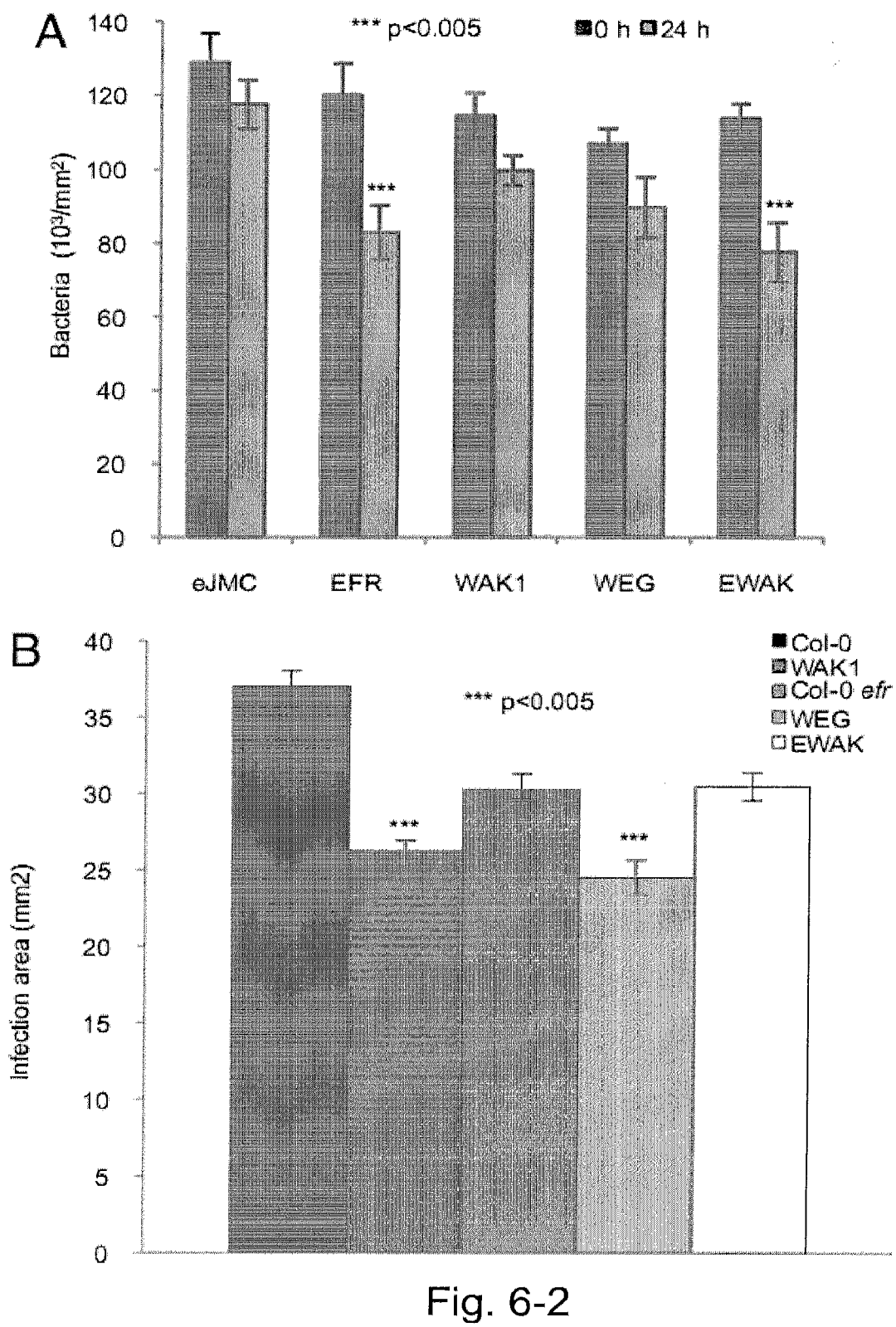
Figures 3, 6:
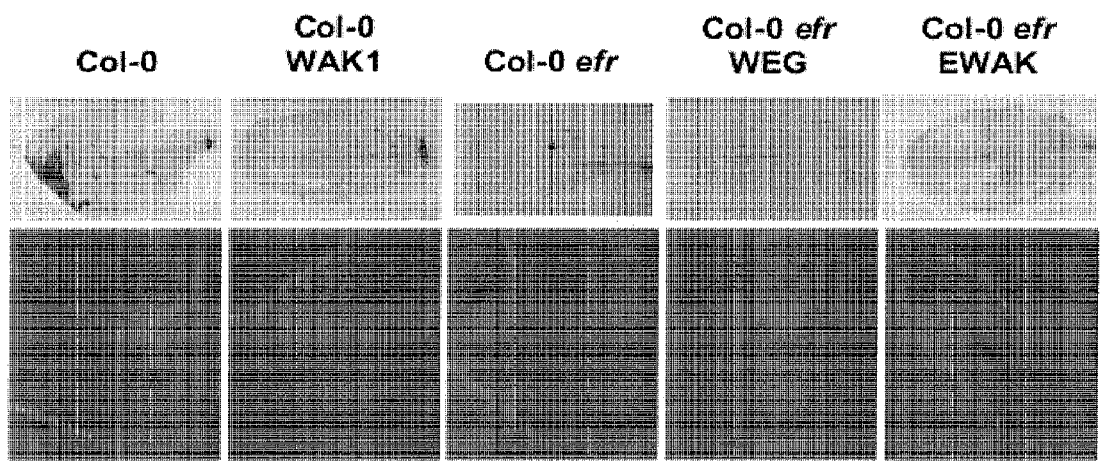
Figures 4, 6:
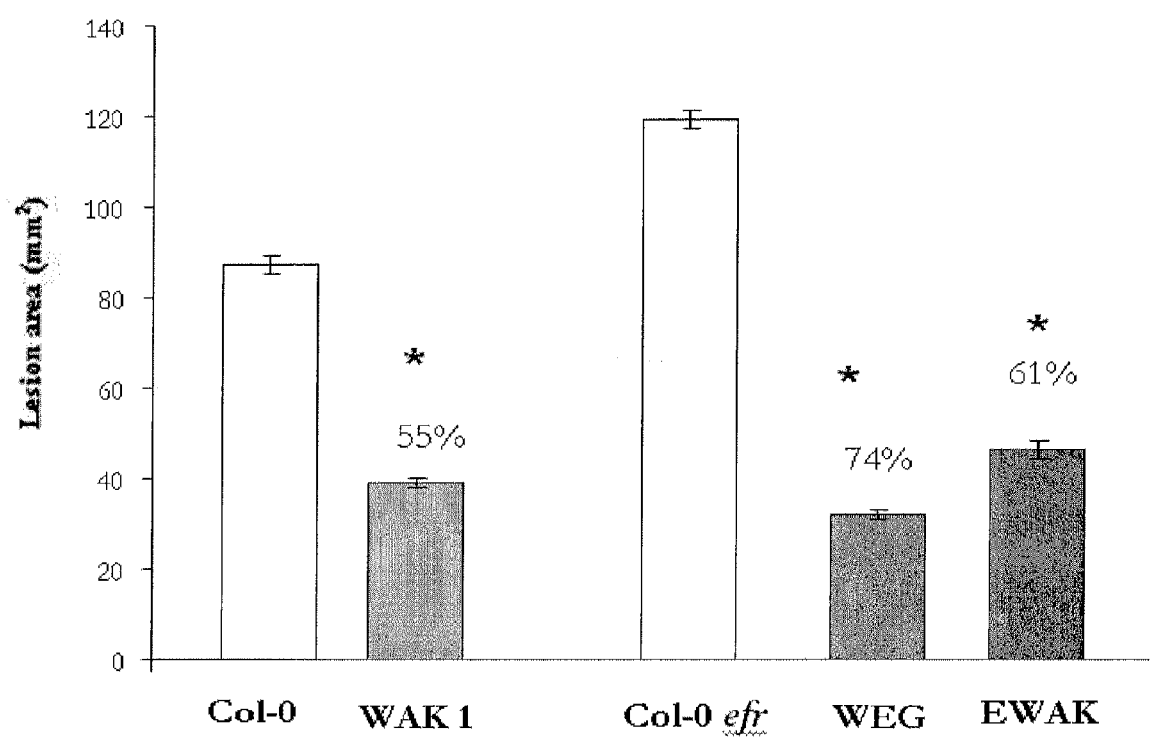

FIG. 6: Transient characterization of WAK1/EFR chimeric receptors

A) Relative variation of fluorescence of WEG-expressing explants treated with H2O or OGs (100 µg/ml). Explants were prepared from leaves 3 days after agroinfiltration. Global fluorescence values evaluated after 20 and 30 min of treatment were normalised against fluorescence measured after 10 min. Error bars indicate the standard error of the three independent replicates.

B) Relative variation of fluorescence in WEG-, WAK1- or FLS2-expressing explants treated for 30 min with elicitors (100 µg/ml OGs, 10 µM flg22, 100 µg/ml 3-6 OGs and 100 µg/mL OMs) and subsequently mounted in the presence of EDTA for confocal microscopy analysis. All values were normalised against global GFP intensity detected after 10 min of stimulation. Error bars indicate the standard error of the three independent replicates.

C) Fluorescence micrographs of merged cross-sections (375 µm×375 µm×20 µm) after a half hour pre-stimulation with OGs (100 µg/ml), and treated with EDTA 5 mM, of agroinfiltrated *Arabidopsis* leaf sectors expressing WEG. The arrows indicate the areas of the tissue showing the decreasing fluorescence signal.

D) Oxidative burst in tobacco leaves transiently expressing eJMC, EFR and EWAK. Photon counting was realized using tobacco leaves slices in a solution of luminol and peroxidase, during treatment with 10 µM elf18. eJMC- and EFR-expressing explants were used as a negative and a positive control, respectively. Experiment was repeated at least 6 times on two independent replicated.

E) Induction of ethylene biosynthesis in agroinfiltrated tobacco leaves expressing EFR, WAK1, WEG and EWAK. Each construct was stimulated for 2 h with elf18 (10 µM) or OGs (100 µg/mL). NC: negative control, represented by agroinfiltrated leaf tissue expressing EFR or FLS2 when OGs or elf18, respectively, were used for elicitation. Error bars indicate the standard error of three independent replicates.

F) Growth of *Agrobacterium* in *N. tabacum* tissues transiently expressing receptor proteins. Tobacco leaves were infiltrated with *Agrobacterium* expressing the indicated receptors and the number of *Agrobacterium* colony-forming units (c.f.u.) in the tissues was analyzed soon after infiltration (white bars) and 24 h (gray bars). EFR and eJMC were used as positive and negative controls, respectively. For each receptor, three samples were analyzed in five independent experiments. *, $p<0.005$.

FIG. 6-1: Induction of defense responses by WAK1/EFR chimeric receptors (A) Induction of ethylene biosynthesis in agroinfiltrated tobacco explants expressing EFR, WAK1, WEG and EWAK. Explants were stimulated for 2 h with elf18 (10 µM) or OGs (100 µg/mL) or short and biologically inactive OGs (OG3-6). Agroinfiltrated leaf tissues expressing EFR or WEG and elicited with OGs or elf18 respectively, represented our negative control. Values are means±s.e.m. (N=3).

(B) Elicitor-induced gene expression in untransformed Col-0 and Col-0 efr plants, and in transgenic *Arabidopsis* Col-0 efr plants stably expressing WEG. Accumulation of At3g22270 and At4g37640 transcripts was analysed by semi-quantitative PCR, using the UBQ5 gene for normalization. Adult leaves were syringe-infiltrated with water, OGs (25 µg/ml) or elf18 (10 µM) for 3 h. The experiment was repeated three times with similar results. The same experiment was performed in a second independent transgenic line expressing WEG with similar results.

(C) Oxidative burst in agroinfiltrated tobacco leaves expressing EWAK. Leaves expressing eJMC and EFR were used as a negative and a positive control, respectively. The burst was measured by photon counting using leaf slices incubated in a solution containing 10 µM elf18, luminol and peroxidase. The experiment was repeated at least 6 times with two independent replicates.

FIG. 6-2: Response to bacterial and fungal pathogens and to OGs of plants expressing the chimeric receptors.

(A) Growth of *A. tumefaciens* in *N. tabacum* tissues transiently expressing receptor proteins. Tobacco leaves were infiltrated with *Agrobacterium* carrying the indicated receptor constructs and the number of *Agrobacterium* colony-forming units (c.f.u.) in the tissues was analyzed immediately after infiltration (white bars) and after 24 h (gray bars). EFR and eJMC were used as positive and negative controls, respectively. For each receptor, three samples were analyzed in five independent experiments. Asterisks indicate statistically significant differences against control (Col-0 for WAK1 plants and Col-0 efr for WEG and EWAK plants). (B) Lesion development in *Arabidopsis* wild type (Col-0) and mutant Col-0 efr plants and in transgenic plants expressing WAK1, WEG and EWAK plants inoculated with *B. cinerea* at 48 h post-inoculation. Values are means±s.e.m. of at least 16 lesions. The same experiment was performed in a second independent transgenic line expressing WAK1 with similar results. Asterisks indicate statistically significant differences against control (Col-0 for WAK1 plants and Col-0 efr for WEG and EWAK plants). No symptoms were observed in plants inoculated with Potato Dextrose Broth (PDB) (mock-inoculation).

FIG. 6-3: Transgenic plants expressing WAK1, WEG and EWAK do not show constitutive activation of defense responses.

Leaves were stained with 3,3'-diaminobenzidine (DAB) for $H_2O_2$ visualization (upper panel) and with aniline blue for callose visualization (lower panel).

FIG. 6-4: Lesion development in *Arabidopsis thaliana* transgenic plants at 24 h after infection with *Pectobacterium carotovorum* subsp. *carotovorum*.

Inoculum concentration was $5 \times 10^7$ CFU/ml). Values are means±SE of at least 16 lesions. Asterisks indicate statistically significant differences against control plants (Col-0 or Col-0 efr), according to Student's t test (*, $p<0.0005$).

Figure 7:
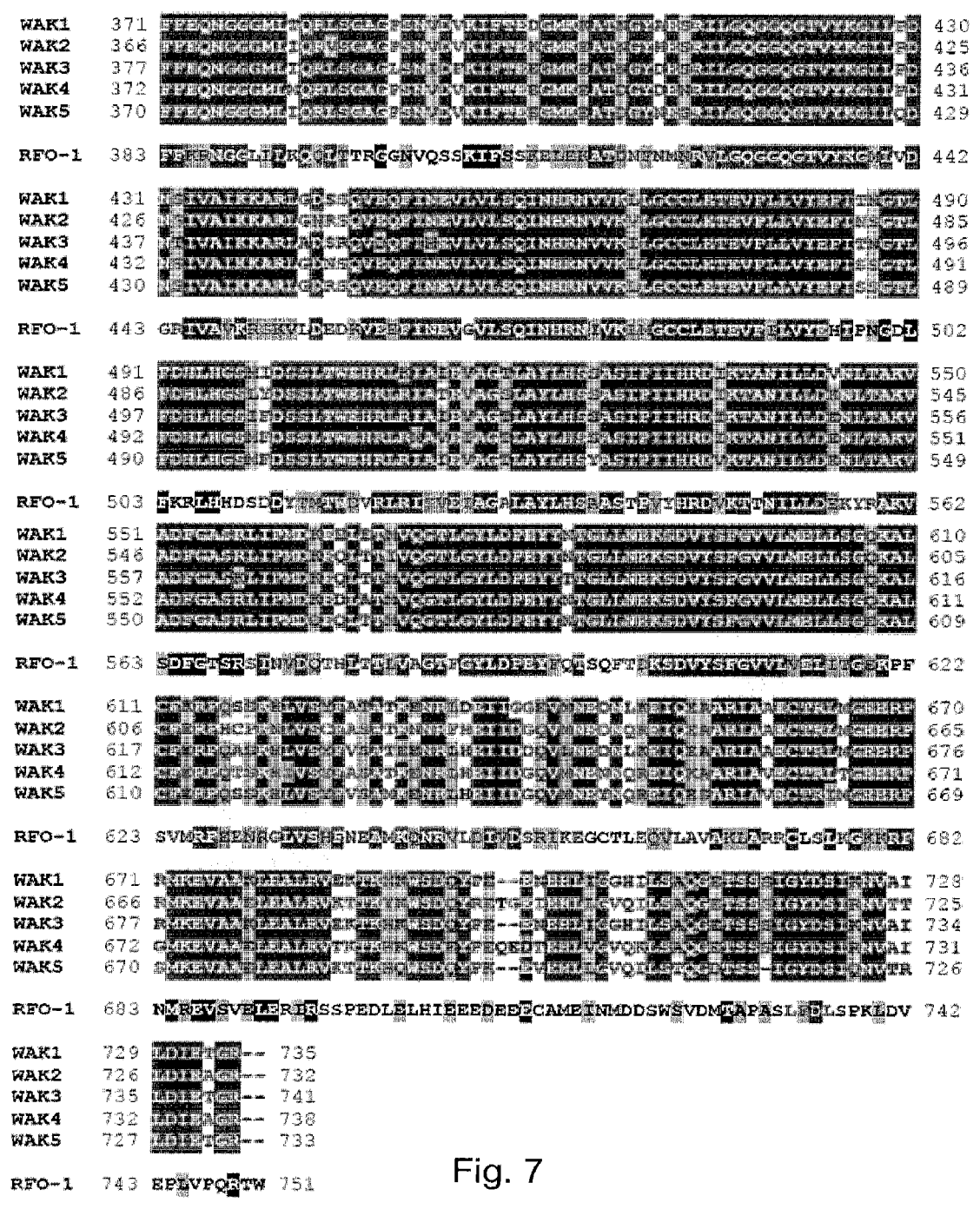

FIG. 7: Sequence alignment of WAK kinases of *A. thaliana*

The sequences are referenced with the corresponding GenBank or SwissProt accession numbers. Figure was prepared with Bioedit (Hall et al., 1999). WAK1 kinase (NP_564137 from 371 to 735; SEQ ID NO: 37) was aligned with WAK2 kinase (NP_173549 from to 732; SEQ ID NO: 38), WAK3 (NP_173547 from 377 to 741; SEQ ID NO: 39), WAK4 (NP_173544 from 372 to 738; SEQ ID NO: 40) and WAK5 (NP_173546 from 370 to 733; SEQ ID NO: 41).The alignment also including RFO-1, the Resistance to *Fusarium Oxysporium* 1(WAKL22: NP_859908 from 383 to 751; SEQ ID NO: 42) (Diener et al., 2005). In black are indicated amino acid identities and in grey the amino acid similarity.

Figure 8:
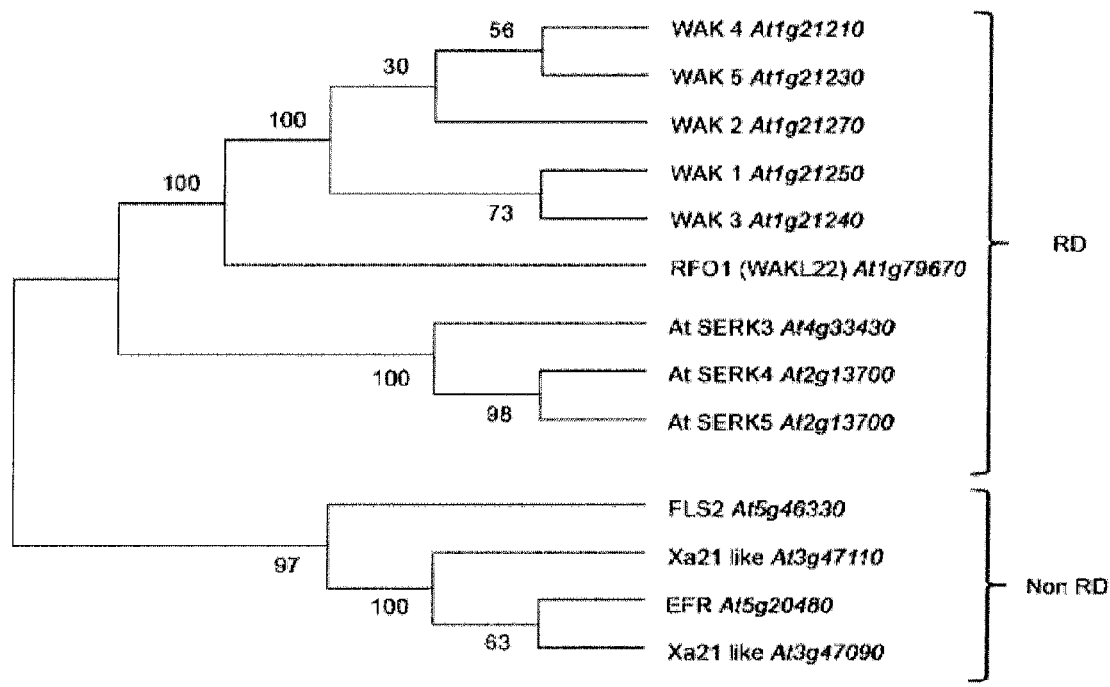

FIG. 8. The kinase of WAK1 is of the RD-type.

Evolutionary relationships of 13 amino acid sequences of RLK kinases from *Arabidopsis thaliana*. The evolutionary history was inferred using the Neighbor-Joining method (Decreux 2006, Kohorn 2009). The bootstrap consensus tree inferred from 10000 replicates is taken to represent the evolutionary history of the kinases analyzed. Branches corresponding to partitions reproduced in less than 50% bootstrap replicates are collapsed. The percentage of replicate trees, in which the associated kinase clustered together in the bootstrap test (10000 replicates), are shown next to the branches. Phylogenetic analyses were conducted in MEGA4 (Wagner 2001). RD and non RD kinases are indicated (Decreux 2005). The observation that, in a survey of the yeast, fly, worm, human, *Arabidopsis* and rice kinomes, 12 of the 15 kinases known to function as pattern recognition receptors (PRRs) in innate immunity are of the non-RD type, whereas the majority of the RD-type is involved in developmental processes, suggests that the RD motif may also characterize kinases that play a role in both defense and development, such as WAK1 and BAK1/SERK3 (Galletti 2008).

EXPERIMENTAL PROCEDURES

Material

The pFLS2::FLS2 and pEFR::EFR were gently provided by Cyril Zipfel (Sainsbury Laboratory, John Innes Center) while bak1.4 knockout line was kindly provided by Delphine Chinchilla (Zurich-Basel Plant Science Center, Botanical Institute, University of Basel). WAK1 cDNA was purchased from ABRC (U09348). OG pools with an average degree of polymerization (DP) of 10 to 15 (OGs) were kindly prepared by Dr. Salvi (Universitàdi Roma "La Sapienza"). Short OG with a DP ranging from 3 to 6, was purchased from Sigma (cat n. T7407). The flg22 and elf18 peptides were synthesized by Pr. Schininà (Universitàdi Roma "La Sapienza") and their sequences have been described by Felix et al. (1999) and Kunze et al., (2004). The sequence of flg22 is QRLSTGSRINSAKDDAAGLQIA (SEQ ID No. 27); while the sequence of elf18 is Ac-SKEKFERTKPHVNVGTIG (SEQ ID No. 28). The peptide, used for a negative control in the gene expression analysis, was kindly provided by Dr. Gianni (Università di Roma "La Sapienza"). This hexapeptide (EQVSAV, SEQ ID No. 29) is involved in the binding of PDZ (Post synaptic density protein (PSD95), Drosophila disc large tumor suppressor (D1gA), and Zonula occludens-1 protein (zo-1)) motif (Jemth P, Gianni S. 2007). *Agrobacterium thumefaciens* GV3101 bacteria carrying the pSOUP helper vector was used for the transformations in plants.

Plant Material

*Arabidopsis* (*Arabidopsis thaliana*) Columbia-0 (Col-0), Wassilewskija-0 (Ws-0) wild-type seeds were purchased from Lehle Seeds. *Arabidopsis* plants were grown on a 3:1 mixture of soil (Einheitserde) and sand (Compo Agricoltura) at 22° C. and 70% relative humidity under a 16-h light/8-h dark cycle (approximately 120 µmol $m^{-2}$ $s^{-1}$). Tobacco (*Nicotiana tabacum*) Petit Havana-SR1 plants were grown in a greenhouse at 23° C. and 60% relative humidity, with a 16-h photoperiod (130 µmol $m^{-2}$ $s^{-1}$).

Cloning and Plant Expression

Standard protocols were used for plasmid DNA isolation, purification and restriction enzyme digestions. As described in by Brutus et al. (2004), all chimeras were generated using the overlap extension method with primers listed in Table 1 and methods summarised in Table 2. Briefly to produce chimera, PCR1 and PCR2 are performed using primers and template listed in Table 2, and following manufacturer indication. Each product from PCR1 and PCR2, are purified and used for PCR3A without primers. Thereafter, primers were added to the PCR3A reaction and run for 25 cycles (PCR3B). All fragments were cloned in pREV-1 (Reca et al., 2008). Constructs were verified by sequencing (Eurofins MWG Operon, Italy). GFP fusion was previously described by (Reca et al., 2008). Site directed mutagenesis, corresponding to Y849A, was achieved using the kit XL-Quick Change (Stratagene).

TABLE 1

Primer list

| NAME | PFOR | PREY | PFOR-SOE | PREV-SOE |
|---|---|---|---|---|
| FLS2 (AT5G46330) | ATGCGGATCCAT GAAGTTACTCTCA (SEQ ID N. 1) | GCATGGTAC CCTACCTAGG AACTTCTCGA TCC (SEQ ID N. 2) | — | — |

TABLE 1-continued

Primer list

| NAME | PFOR | PREY | PFOR-SOE | PREV-SOE |
|---|---|---|---|---|
| EFR (AT5G20480) | (1) (SEQ ID N. 3) ATGCGGATCCAT GAAGCTGTCCTTT TC<br>(2) (SEQ ID N. 4) ATCGGAATCCAT GAAGCTGTCCTTT TCAC | GCATGGTAC CCTACCTAGG GCATACTATG TAG (SEQ ID N. 5) | — | — |
| TMC | — | — | ATTCTTGGATCAGCCGCG GCTCTTTTGTTAATCATAA TTGT (SEQ ID N. 6) | ACAATTATGATTAACAAA AGAGCCGCGGCTGATCCA AGAAT (SEQ ID N. 7) |
| eJMC | — | — | TTCTCGAAGAGAACCAGA GTTGTCAGTGGTATTTGTA TAG (SEQ ID N. 8) | CTATACAAATACCACTGA CAACTCTGGTTCTCTTCGA GAA (SEQ ID N. 9) |
| WAK1 (AT1G21250) | (1) (SEQ ID N. 10) ATGCGAATCCAT GAAGGTGCAGGA GGG<br>(2) (SEQ ID N. 11) ATGCCCGGGATG AAGGTGCAGGAG GG | GCATGGTAC CCTACCTAGG GCGGCCAGT TTCAATG (SEQ ID N. 12) | | |
| WEG | — | — | CTGCAAGCGTAAAGAGTT TGCAGTTGTCAGTGGTATT TGTAT (SEQ ID N. 13) | ATACAAATACCACTGACA ACTGCAAACTCTTTACGCT TGCAG (SEQ ID N. 14) |
| EWAK | — | — | GCCTCTGTCAGTTAGAAA GAAATGGACTACAATTCT TCTTGG (SEQ ID N. 15) | CCAAGAAGAATTGTAGTC CATTTCTTTCTAACTGACA GAGGC (SEQ ID N. 16) |
| eJMC$^{Y859A}$ | CTTTGGGGATGTT CCATGAGAAGGT AAGTGCTGAAGA GCTTCATAG (SEQ ID N. 17) | CTATGAAGCT CTTCAGCACT TACCTTCTCA TGGAACATC CCCCAAAG (SEQ ID N. 18) | | |
| UBQ5 (AT1G62250) | GGAAGAAGAAGA CTTACACC (SEQ ID N. 19) | AGTCCACACT TACCACAGT A (SEQ ID N. 20) | | |
| RetOx (AT1G26380) | CGAACCCTAACA ACAAAAAC (SEQ ID N. 21) | GACGACACG TAAGAAAGT CC (SEQ ID N. 22) | | |
| CYP81F2 (AT5G57220) | GTGAAAGCACTA GGCGAAGC (SEQ ID N. 23) | ATCCGTTCCA GCTAGCATC A (SEQ ID N. 24) | | |
| PAD3 (AT3G26830) | TCGCTGGCATAA CACTATGG (SEQ ID N. 25) | TTGGGAGCA AGAGTGGAG TT (SEQ ID N. 26) | | |

TABLE 2

Scheme of the amplifications

| Gene product | PCR 1 | PCR 2 | PCR 3A | PCR 3B | Restriction site for cloning (5' site/3' site) |
|---|---|---|---|---|---|
| FLS2 | pFw-FLS2 pRev-FLS2 30 cycles pFLS2::FLS2 | — | — | — | BamHI/KpnI |

TABLE 2-continued

Scheme of the amplifications

| Gene product | PCR 1 | PCR 2 | PCR 3A | PCR 3B | Restriction site for cloning (5' site/3' site) |
|---|---|---|---|---|---|
| EFR | pFw-EFR1 prev-EFR 30 cycles pEFR::EFR | — | — | — | BamHI/KpnI |
| TMC | pFw-FLS2 pRev-SOE-TMC 30 cycles pFLS2::FLS2 | pFw - SOE-TMC pRev -EFR 30 cycles pEFR::EFR | 5 cycles TMC-PCR 1 TMC-PCR 2 | pFw -FLS2 pRev -EFR 25 cycles TMC-PCR 3A | BamHI/KpnI |
| eJMC | pFw-FLS2 pRev-SOE-eJMC 30 cycles pFLS2::FLS2 | pFw -SOE-eJMC pRev -EFR 30 cycles pEFR::EFR | 5 cycles eJMC-PCR 1 eJMC-PCR 2 | pFw -FLS2 pRev -EFR 30 cycles eJMC-PCR3 A | BamHI/KpnI |
| WAK1 | pFw-WAK1A pRev-WAK1 30 cycles WAK1 cDNA | — | — | — | EcoRI/KpnI |
| WEG | pFw-WAK1B pRev-SOE-WEG 30 cycles WAK1 cDNA | pFw -SOE-WEG pRev -EFR 30 cycles pEFR::EFR | 5 cycles WEG-PCR 1 WEG-PCR 2 | pFw -WAK1B pRev -EFR 25 cycles WEG-PCR 3A | SmaI/KpnI |
| EWAK | pFw-EFR2 pRev-SOE-EWAK 30 cycles pEFR::EFR | pFw -SOE-EWAK pRev -WAK1 30 cycles WAK1 cDNA | 5 cycles EWAK-PCR 1 EWAK-PCR 2 | pFw -EFR2 pRev -WAK1 25 cycles EWAK-PCR 3A | EcoRI/KpnI |

To obtain the chimeric genes, amplifications (PCR1 and PCR2) were performed using the indicated primers and templates. Each product from PCR1 and PCR2 was purified and used for a primer-less PCR3A. Next, primers were added to the PCR3A reaction for PCR3B. Templates for PCR are in bold.

PCR templates are shown in bold. Primers listed in Table 1 are shown in capital letters. Stable transgenic lines were generated using the standard *A. tumefaciens*-mediated gene transfer procedure of inflorescence infiltration (Bent et al., 2006). Independent transformed plant pools were kept separate for the selection of independent transgenic lines based on their phosphinotrycin resistance and leaves GFP fluorescence. Tobacco and *Arabidopsis* transient transgenic lines were prepared by infiltrating with *Agrobacterium tumefaciens* carrying the individual constructs, as described by Reca (2008).

Agrobacterium tumefaciens Infections

*Agrobacterium tumefaciens* GV3101 strain infections was performed as described in Katagiri et al., (2002) and using a concentration of *Agrobacterium* corresponding at an $OD_{600}$ of 1.0 in 10 mM $MgCl_2$ and 600 µM acetosyringone. After 24 h of infiltration, serial dilution of *Agrobacterium* colonies were deposited on LB agar supplemented with gentamycin and rifampicin and grown for 2-3 days at 28° C. in the dark. At least 5 independent plants and 3 different leaves by plant, were used per experiment. *Pectobacterium carotovorum* subsp. *carotovorum* infections *Pectobacterium carotovorum* subsp. *carotovorum* (formely *Erwinia carotovora*; Gardan et al., 2003) (strain DMSZ 30169) was obtained from DSMZ GmbH (Germany). A liquid colture using 10 ml LB medium was prepared. After 16 h of growth at 28° C. on rotary shaker at 250 rpm, bacterial cells were harvested by centrifugation and the pellet was resuspended in 50 mM potassium phosphate buffer pH 7.0 corresponding to $5 \times 10^7$ CFU/ml.

For infection, fully developed leaves of 4 week old *Arabidopsis* plants were detached and placed in 0.8% agar Petri dishes. A small hole was made with a needle on each half leaf and 5 µA of bacterial drop suspension was spotted. Symptoms were scored measuring the area of macerated tissue after 24 hour post inoculation at 22° C. and 12 h photoperiod. Area was measured by ImageJ software. The experiments was repeated three times and statistical analysis was performed by one way ANOVA followed by Tukey's student's range.

Confocal Microscopy

The GFP-dependent fluorescence was monitored from 2 to 4 days post infection in cells of the lower epidermis. Pieces of leaf were randomly cut from the infected area and mounted in water or supplemented with elicitors for microscopic observations. Flg22 and elfl8 were used at 10 µM while oligosaccharides were used at 100 µg/mL. Materials were analyzed using a Leica DM IRE epifluorescence microscope equipped with a digital cooled camera (DFC350FX R2; Leica). GFP fluorescence was excited with a 488-nm laser line, and emitted fluorescence was collected at 543-nm. The Leica Confocal Software and Adobe Photoshop 5.0 were used for post-acquisition image processing. All samples were imaged with the 40× or 100× oil objectives. Pictures were taken in Kahlman frame giving an average of 16 scans for the dynamics of internalization and 4 scans for the cellular localizations.

Protein Extraction from Plants

*Arabidopsis* or tobacco leaves Agro-infiltrated with the corresponding constructs were used to prepare crude extracts, microsomal fractions and intercellular washing fluids. Total extracts were prepared as described by Chinchilla et al. (2007); microsomal and intercellular washing fluids were prepared as described by Sicilia et al. (2005). Total protein concentration was determined by the Bradford method (Bradford, 1976). Expression of the different GFP fused proteins were confirmed by Western blot analysis using anti-GFP polyclonal antibodies (Santa Cruz Biotechnology) and detected using ECL kit (Amersham).

Ethylene Measurements

Approximately 150 mg of tobacco agroinfiltrated leaf were cut in small slices and extensively washed with sterile distilled water. The explants were placed in sealed 10 mL flasks containing 2 mL of sterile water alone or supplemented with 100 mg $L^{-1}$ OGs, or 1 µM flg22 or 10 µM elfl8. 450 µl headspace samples were withdrawn from the vial after 2 h treatment and analyzed by gas chromatography-mass spectrometry using an Agilent 6850A gas chromatograph coupled to a 5973N quadrupole mass selective detector (Agilent Technologies, Palo Alto, Calif., USA). Chromatographic separations were carried out an HP Plot-Q fused-silica capillary column (30 m×0.32 mm i.d.) coated with polystyrene-divinylbenzene (film thickness 0.20 µm) as stationary phase. Injection mode: splitless at a temperature of 220° C. The initial temperature of the oven was held at 50° C. for 8 min then ramped to 220° C. at a rate of 15°

C./min and held for 5 min. Helium was used as carrier gas at a constant flow of 1.0 ml/min. Mass spectra were collected both in full scan and in SIM mode monitoring the ions m/z m/z 26, m/z 27 and m/z 28 (ionization energy 70 eV; ion source 280° C.; ion source vacuum $10^{-5}$ Torr).

Bioassays with Plant Tissue 3,3'-diaminobenzidine (DAB) staining, callose deposition and gene resistance analysis were assayed as described (Galletti et al., 2008). For measuring active oxygen species released by tobacco agroinfiltrated plants after elicitor treatment, the authors used a modified luminol-dependent assay (Gomez et al., 1999). Slices, corresponding to approximately 30 mg fresh weight, were transferred to assay tubes containing 1 µM flg22 or 10 µM elf18 in aqueous solution supplied with 40 µM luminol (SIGMA). Chemo-luminescence was measured in a liquid scintillation counter (LS-6500, Beckman) after 5 and 15 min upon addition of elicitors.

Statistical Analysis. Data are represented as means±standard error (s.e.m.). Unpaired t-test with equal variance was used to calculate two-tailed P value to estimate statistical significance of differences between two treatment groups in the whole study. Assays were run in duplicate or triplicate and repeated in a minimum of three independent trials.

Results

Design of a Functional FLS2/EFR Chimeric Receptor

Two chimeric genes named TMC and eJMC comprising the extracytosolic portion of FLS2 and the intracytosolic portion of EFR were constructed (FIG. 1A). The chimeric receptors differed from each other and from those previously tested in plants (He et al., 2000; Cao et al., 2007a) in the junction point. The chimera TMC (Ala817$_{FLS2}$-Leu661$_{EFR}$) included the leucine-rich repeat (LRR) domain, the external juxtamembrane (eJM) domain and the N-terminal half of the transmembrane (TM) domain of FLS2 which is fused upstream of the C-terminal half of the EFR TM domain, excluding the putative dimerization consensus sequence WOW, and the iJM and kinase domains of EFR (FIG. 1B). The chimera eJMC (Arg806$_{FLS2}$-Val650$_{EFR}$) included the LRR and eJM domains of FLS2 fused upstream of the entire transmembrane domain (TM), iJM and kinase domains of EFR. Both chimeric receptors, as well as FLS2 and EFR as controls, were fused to GFP to allow detection by confocal microscopy and Western blot analyses. The genes encoding the four protein fusions were each cloned in the pREV1 vector, a pGREEN0229 modified vector (Reca et al., 2008), under the control of the CaMV 35S and NOS terminator.

The functional characterization of the fluorescent protein fusions was performed in a transient expression system, using *Arabidopsis thaliana* (ecotype Col-0) leaves infiltrated with *Agrobacterium tumefaciens* carrying the individual constructs. At two days post-infiltration (dpi), total protein extracts were prepared from infiltrated leaves and subjected to Western blot analysis using a GFP-specific polyclonal antibody. A specific band with a mobility close to that previously reported for FLS2 (Robatzek et al., 2006), apparent molecular mass of ~170 kDa) was visible in the protein extracts from leaves agroinfiltrated with the four constructs (FIG. 2A). Confocal microscopy analysis of the agroinfiltrated leaves showed comparable levels of fluorescence, which was localized in correspondence of the plasma membrane (FIGS. 2B and C), for all the protein fusions. Dot-blot analysis using the GFP antibody of the microsomal fractions and intercellular washing fluids (IWF) confirmed the plasma membrane localization of the proteins (FIG. 2D).

The dynamics of fluorescence localization upon treatment with elicitors was then studied. Whereas endocytosis of surface receptors upon ligand binding often occurs in animals (Warren and Landgraf 2006), this mechanism in plants has emerged only recently (Geldner & Robatzek 2008) and, so far, FLS2 is the only receptor involved in plant immunity shown to undergo endocytosis upon the specific stimulation with flg22 (Robatzek et al., 2006). The authors tested the effect of flg22 and elf 18, i.e. the peptides specifically recognized by FLS2 and EFR respectively, and oligogalacturonides with a degree of polymerization between 10 and 16 (OGs), which act as general elicitors of defense responses in several plants. Explants from agroinfiltrated *Arabidopsis* leaves at 2 dpi were treated with elicitors and then subjected to confocal microscopy analysis. No decrease of the plasma membrane-associated fluorescence signal was observed in non-elicited leaf sectors expressing FLS2, while flg22-treated tissues showed a 15% and 30% decrease after 20 min and 30 min of stimulation, respectively (FIG. 3A). The fluorescence decrease did not involve the entire infiltrated sector but only patches, probably due to the heterogeneous penetration and/or diffusion of flg22 (FIG. 3B). Instead, elf18-treated leaves expressing EFR showed no significant decrease of fluorescence (FIG. 3A), up to a concentration of 1 mM elicitor (data not shown). Similarly, TMC-expressing leaves did not show any decrease in fluorescence upon treatment with flg22. Instead, when eJMC-expressing explants were stimulated with flg22, the fluorescent signal decreased by 25% and 40% after 20 min and 30 min, respectively (FIG. 3B). Treatment of eJMC-expressing explants with elf18 and elicitor-active OGs did not induce any significant fluorescence variation.

The decrease of fluorescence in eJMC-expressing explants in response to flg22 may be due to an endocytosis mechanism similar to that demonstrated in FLS2 and depending on the occurrence of the PEST-like motif in its C-terminal region, between Arg1090 and Leu 1105 (Hammond et al., 2001). The PEST-like motif is absent in eJMC which contains instead the tyrosine tetrapeptide YXXΦ (Husebye et al., 2006) originally present in EFR (residues 859-862) (Zipfel et al., 2006; Robatzek et al., 2006). In order to verify whether this tetrapeptide is responsible for decrease of fluorescence in flg22-treated eJMC-expressing explants, a variant mutated in the first amino acid of the YXXΦ sequence (eJMC$^{Y859A}$) was obtained and its behaviour upon stimulation with flg22 was analysed by confocal microscopy in agroinfiltrated explants. Fluorescence levels did not decrease upon stimulation with either 10 or 100 µM flg22 (FIG. 3C), suggesting that decrease of fluorescence is likely due to internalisation of the protein mediated by YXXΦ.

The authors also tested whether the presence of the LRR-RLK BAK1 (Nam & Li 2002), a protein required for flg22 and elf18 signalling (Chinchilla et al., 2007), is also required for the internalization of eJMC induced by flg22. Internalization of flg22 was nearly abolished in the bak1-4 mutant; instead, that of eJMC induced by flg22 was not affected (FIG. 3D). These data demonstrate that while the internalization of FLS2 depends on the presence of BAK1, the internalization of the eJMC chimera does not.

The behaviour of TMC and eJMC upon treatment with flg22 and elf18 was also analysed in agroinfiltrated leaves of *N. tabacum* ecotype SR1 and compared to that of EFR and FLS2. Confocal microscopy analysis of infiltrated leaf sectors at 2 dpi showed similar levels of fluorescence and similar pattern of localization at the level of the plasma membrane of all the expressed protein fusions (data not shown). Neither FLS2 nor TMC underwent internalization after stimulation with flg22; similarly, EFR showed no response upon stimulation with elf18. Instead, in the eJMC expressing plants fluorescence decreased within 10-30 min after stimulation with flg22, at an extent similar to that observed in *Arabidopsis*, i.e. by 25% and 35% after 20 min and 30 min, respectively (FIG. 3E).

Expression of eJMC Confers to Plants the Ability of Activating the Typical Defense Responses of EFR Upon Treatment with flg22.

In order to characterize the chimeric receptors and their ability to activate downstream defense responses, ethylene production, known to be activated by FLS2 and EFR in response to flg22 and elf18, respectively (Zipfel et al., 2006; Robatzek et al., 2007), was monitored in agroinfiltrated tobacco leaf explants separately expressing fluorescent FLS2, EFR, TMC, eJMC or eJMC$^{Y859A}$ (FIG. 3F). Levels of ethylene were slightly higher in non-elicited agroinfiltrated explants leaves than in non-infiltrated ones (FIG. 3-1), and slightly increased in response to flg22, but not to elf18, in both types of explants, indicating an intrinsic weak ability of *N. tabacum* to respond to flg22. On the other hand, in EFR-expressing explants elf18 induced a release of ethylene 3.8 times higher than in FLS2-expressing explants (negative control), confirming the previous observations that EFR is functional in tobacco (Zipfel et al., 2006). In eJMC-expressing explants, flg22 induced an ethylene release significantly higher than in EFR-expressing explants used as negative controls, whereas both TMC- and FLS2-expressing explants showed only a weak response to this elicitor. This result is in agreement with the observation that FLS2 is not functional in *Nicotiana benthamiana* (Zipfel et al., 2004; Robatzek et al., 2007). Notably, ethylene accumulation induced by flg22 in eJMC$^{Y859A}$ expressing explants was 4.8 times higher than that in the negative control, suggesting that mutation of the YXX motif impedes internalization of the receptor but not the kinase activation and the subsequent response.

Fluorescent eJMC and FLS2 were also stably expressed in transgenic *Arabidopsis* ecotype Wassilewskija (Ws-0), which carries EFR but lacks a flg22 perception system (Gomez-Gomez et al., 1999, Bauer et al., 2001). Transformed T1 plants expressing the proteins, named eJMC plants and FLS2 plants, respectively, were selected by confocal microscopy analysis of adult rosette leaves. Two independent positive lines (#1.4 and 1.6) for eJMC plants and one for FLS2 plants, showing comparable levels of fluorescence, were chosen for further analyses. However, transgenic T2 seedlings of the three lines exhibited antibiotic-resistance but no fluorescence in different organs during plant growth. Fluorescence was detected only in adult rosette leaves, likely due to a low expression level of the receptor at the different developmental stages. Probably as a consequence of the low level of eJMC and FLS2, transgenic seedlings did not show growth inhibition (Gomez-Gomez et al., 1999) when treated with flg22 (data not shown). Flg22 induced $H_2O_2$ production and callose deposition in both FLS2 (data not shown) and eJMC plants, but not in untransformed Ws-0 plants; the latter instead responded to elf18 (FIG. 4A). Similarly, the expression of three genes potentially involved in pathogen resistance, i.e. a putative reticuline oxidase gene (RetOx; At1g26380), the cytochrome P450 gene ATCYP81F2 (At5g57220) and PAD3 (At3g26830), which encodes the last enzyme of the camalexin biosynthetic pathway (Ferrari et al., 2007), was induced by flg22 in both FLS2 and eJMC, but not in the untransformed plants (FIG. 4B). These results confirm the functionality of the chimeric receptor eJMC.

The authors therefore infected *A. thaliana* plants by spraying Pst DC3000 bacteria onto leaf surfaces. Under these conditions, Ws-0 plants showed a faster and more severe development of disease symptoms than FLS2 or eJMC plants (FIG. 4C). These stronger symptoms correlated with higher numbers of bacteria in Ws-0 than in FLS2 or eJMC leaves (FIG. 4C). Higher resistance of eJMC plants, compared to Ws-0 wild-type plants, was found in all of three independent experiments.

Ws-0 plants transformed with a functional eJMC gene, acquired responsiveness to flg22 and became less susceptible to Pst DC3000, indicating that the natural deficiency in flagellin perception in the ecotype Ws-0 can be complemented with the chimeric eJMC gene.

Design of WAK1/EFR Chimeric Receptors and Identification of WAK1 as a Receptor of Oligogalacturonides.

Following the demonstration that the chimeric receptor FLS2/EFR is functional, the design strategy utilized above was used to construct two additional chimeras, with the aim of investigating whether WAK1, an RLK without a defined biological function but known to interact with the pectin component of the extracellular matrix, is a receptor for OGs (FIG. 5A). The first chimeric receptor, indicated as WEG, comprised the WAK1 ectodomain fused to the TM-iJM-kinase portion of EFR and was designed to test the ability of the WAK1 ectodomain to perceive OGs and transmit the signal inside the cell. A second chimera, indicated as EWAK, comprising the EFR ectodomain fused to the TM-iJM-kinase portion of WAK1, was designed to ascertain whether the responses downstream of the elf18-mediated activation of the WAK1 kinase are related to those normally induced by OGs. Both WEG and EWAK as well as WAK1 were fused to GFP and used in agroinfiltration experiments (FIG. 5A). Confocal microscopy analysis of the agroinfiltrated explants showed that the fluorescence deriving from EWAK, WEG and WAK1 was localized in correspondence of the plasma membrane, at similar levels as those observed for FLS2 e EFR (FIGS. 5B, 5C). Western-blot analysis using GFP-specific antibodies on proteins from IWF and microsomal fractions prepared from infiltrated leaves confirmed the plasma membrane localization of both fluorescent chimeras (FIG. 5D). The effect of OGs on the internalization of WEG was followed in agroinfiltrated *Arabidopsis* Col-0 leaves. No decrease of the plasma membrane-associated fluorescence was detected up to 30 min after treatment with OGs (FIG. 6A). This might be due to the inability of WEG to uncouple its ectodomain from pectins, since it is known that WAK1 strongly binds to pectin and only denaturing treatments allow its separation from cell wall (He et al., 1996). On the other hand, affinity studies have shown that WAK1 interact with cell wall pectins that are in a $Ca^{2+}$-induced conformation (i.e. the structures called "egg boxes") and that the interaction is disrupted by adding a chelating agent such as EDTA (Decreux et al., 2005; Cabrera et al., 2008). The authors therefore tested whether OG-induced internalization of WEG occurred in the presence of 5 mM EDTA. WEG-expressing agroinfiltrated leaves were syringe-infiltrated with OGs and after 30 min the tissues were mounted in the presence of EDTA for confocal microscopy analysis. In these conditions, WEG fluorescence decreased from the cell membrane by 15% and 25% after 20 min and 30 min, respectively. No decrease of fluorescence was observed in the presence of EDTA upon stimulation of either WEG with flg22 or WAK1 or FLS2 with OGs, ruling out a non-specific activation of endocytosis by EDTA or elicitors (FIGS. 6B and 6C). Internalization of WEG in the presence of EDTA did not occur upon stimulation with OGs with a degree of polymerisation between 3 and 6 (3-6 OGs) and oligomannuronides (OMs), two classes of oligosaccharides known to be biologically inactive.

The ability of WEG to activate downstream defense responses upon stimulation with OGs was analysed by measuring ethylene production, which is not normally induced by OGs in both tobacco and *Arabidopsis* (Ferrari et al., 2007); see also FIG. 3F) but is expected to be induced upon activation of kinase domain of EFR. Agroinfiltrated tobacco leaves expressing WEG accumulated ethylene when treated with OGs, at a level significantly higher (2.4 times) than that of the negative control, i.e. OG-stimulated EFR-expressing tissues (FIG. 6F).

In summary the ectodomain of WAK1 was able to sense specifically the presence of OGs and to transmit a signal inside the cell.

Following the demonstration that the WAK1 ectodomain is able to sense OGs the authors investigated whether the WAK1 kinase domain is able to activate a specific response normally activated by OGs in plants. Induction of the oxidative burst and ethylene production were analysed in agroinfiltrated EWAK-expressing tobacco leaves upon elicitation with elf18. Tissues expressing eJM and EFR were used as a negative and a positive control, respectively. Like EFR-expressing explants, EWAK-expressing tissues produced an oxidative burst after 15 min of treatment with elf18, while eJM-expressing explants did not show any significant response (FIG. 6E). On the other hand EFR-expressing explants accumulated ethylene upon stimulation with elf18, whereas or EWAK- and eJM-expressing tissues did not (FIG. 6F). The inability of EWAK-expressing tissues to activate ethylene production and their ability to activate the oxidative burst is in agreement with the observation that OGs do not elicit ethylene synthesis but normally induce the oxidative burst in plant tissues (FIG. 3F).

The ability of WEG to activate downstream responses upon stimulation with OGs was analysed in agroinfiltrated tobacco. Treatment with OGs induced a higher ethylene accumulation (2.4 times) in WEG-expressing explants than in negative controls, i.e. EFR-expressing tissues treated with OGs and WEG-expressing tissues treated with short and biologically inactive OGs (OG3-6) (FIG. 6-1A). Furthermore, the functionality of WEG was analyzed upon expression in transgenic Col-0 efr plants by monitoring the expression of two genes (At3g22270 and At4g37640) that are up-regulated by flg22 and elf18 but not by OGs (Denoux 2008, Zipfel 2006). No constitutive activation of the expression of these genes was observed in the transgenic plants (see water controls in FIG. 6-1B). After a 3 h treatment, both genes were up-regulated by elf18 and not by OGs in wild type Col-0 and did not respond to elf18 in the efr mutant, as expected, while in WEG transgenic plants both genes were induced by OGs but not by other elicitors (FIG. 6-1B). These results show that WEG induces an EFR-type response upon sensing OGs.

Conversely, the EWAK chimera allowed us to investigate whether the WAK1 kinase domain activates the specific responses normally activated by OGs. Upon elicitation with elf18 of tobacco agroinfiltrated leaves, expression of both EWAK and EFR, but not of eJMC, was associated to a robust oxidative burst (FIGS. 6 D and 6-1C); on the other hand, while EFR-expressing explants treated with elf18 accumulated ethylene, tissues expressing EWAK or eJMC used as a negative control did not (FIG. 6-1A). Two hallmarks of the response to OGs, i.e. the occurrence of a robust oxidative burst and the absence of ethylene induction, were therefore observed upon specific activation of EWAK. As tobacco, like *N. benthamiana*, acquires responsiveness to elf18 only upon expression of EFR, and this receptor, but not FLS2, recognizes *A. tumefaciens* and restricts its growth (Zipfel 2006), we investigated whether the expression of EWAK affects *Agrobacterium* survival in the tissues. A 30% decrease (p<0.005) in the number of living *Agrobacterium* cells was observed 24 h after inoculation in tissues expressing EFR or EWAK, while no significant effect was observed in tissues expressing eJMC, WAK1 or WEG (FIG. 6-2A). These results indicate that *Agrobacterium*-induced activation of the WAK1-derived kinase of EWAK triggers defense responses that restrict colonization by this bacterium. The kinase of WAK1, like that of BAK1/SERK3 and WAKL22, is of the RD-type (FIG. 8), i.e. it carries a conserved arginine (R), immediately preceding the invariant aspartate (D) in the catalytically-active subdomain VI and required for the activation of the kinase through an autophosphorylation of a regulatory region termed the activation loop (Ferrari 2008). The observation that, in a survey of the yeast, fly, worm, human, *Arabidopsis* and rice kinomes, 12 of the 15 kinases known to function as pattern recognition receptors (PRRs) in innate immunity are of the non-RD type, whereas the majority of the RD-type is involved in developmental processes, suggests that the RD motif may also characterize kinases that play a role in both defense and development.

WAK1 and WEG, but not EWAK, plants showed increased resistance to *B. cinerea* infection compared to wild type controls (Col-0 or Col-0 efr) (FIG. 6-2B), in agreement with previous studies showing that OG perception plays a role in resistance against *B. cinerea* (Ferrari 2007). Since none of the transgenic plants showed constitutive activation of defense responses, as determined by the analysis of $H_2O_2$ levels and callose deposits (FIG. 6-3), these data suggest on the one hand that both the WAK1 and the EFR kinase domains induce responses effective against this fungus and, on the other hand, that Botrytis does not activate the EFR ectodomain to an extent sufficient to reduce its growth.

Infection Assay with *Pectobacterium carotovorum* on Transgenic Plants Expressing WAK1 or the Chimeric Receptors WEG and EWAK Transgenic plants expressing singularly the fluorescent receptors WAK1, WEG and EWAK under the control of the CaMV 35S promoter showed increased resistance to *Pectobacterium carotovorum* subsp. *carotovorum* (formerly *Erwinia carotovora*; Gardan et al., 2003) compared to untransformed controls (Col-0 or Col-0 efr) (FIG. 6-4). Because none of the transgenic plants showed constitutive activation of defense responses, as determined by the analysis of $H_2O_2$ levels and callose deposition, these data indicate that both the WAK1 and the EFR kinase domains are capable of inducing responses effective against this bacterium. They also show that both chimeras WEG and EWAK confer resistance to *Pectobacterium carotovorum*.

DISCUSSION

Validation of the Approach Utilizing EFR-Based Chimeric Receptors

The construction of chimeric receptors represents a unique tool for elucidating the function of orphan or functionally redundant receptors and has been widely used in animal biology to provide a deep insight into the mechanisms of signal perception. In plants, however, very little progress has been made using this approach and since the first report on BRI1/Xa21 chimeras (He et al., 2000), relevant information was gained only when domain swapping were performed on very closely related homologous receptors (Wulff et al., 2001; Van der Hoorn et al., 2005; Rairdan & Moffett 2006). Notwithstanding, the authors decided to utilize a chimeric receptor approach to investigate whether the receptor kinase WAK1, shown to bind OGs and homogalacturonan, is involved in perception and transduction of the OG signal. The PAMP LRR receptor kinases EFR of *Arabidopsis* was chosen as a recipient protein structure because, unlike FLS2, functions both in *Arabidopsis* and in *N. benthamiana* (Zipfel et al., 2006; Chinchilla et al., 2007; Robatzek et al., 2007). Since FLS2 and EFR are related and activate responses overlapping by more than 98% (Zipfel et al., 2006), the authors initially designed a proof-of-concept experimental procedure and tested whether a functional chimera could be obtained by using the extracellular domain of FLS2 and the kinase domain of EFR. For the construction of the chimeras, the authors chose a design different from that previously utilized, where the ectodomain-TM-iJM portion of one receptor was fused to the kinase domains of a second receptor (He et al., 2000; Cao et al., 2007b). The authors hypothesised that a design that maintains the integrity of the iJM-kinase portion of a receptor is more amenable to provide fully active chimeric receptors; in fact, the iJM region of BRI1 and other receptors has been found to be autophosphorylated at multiple sites, and it has been proposed that this autophosphorylation might indicate multiple, interacting cytoplasmic partners for the receptor, each with a specific phosphorylated target sequence (Oh et al., 2000).

In the design exemplified by eJMC, the entire extracellular domain of FLS2 was fused to the TM-iJM-kinase portion of EFR. A fusion based on a similar design was used to study the Drosophila Toll-related receptors (Tauszig et al., 2000) and the rainbow trout Toll-Like Receptors (TLR) (Tsujita et al., 2004). On the other hand, the design of the TMC chimera aimed at testing whether the integrity of the EFR TM helical domain and a putative TM dimerization consensus sequence (GXXXG) (Mendrola et al., 2002), present in EFR and absent in FLS2 (Ali et al., 2007), is important for the functionality of the chimera. In animals, TM domains have been shown to play an important role in the ligand-dependent dimerization and activation of several receptors (Bennasroune et al., 2005; Bocharov et al., 2008), whereas in other cases may induce a dimerized inactive state of the receptor in the absence of the ligand that may be more readily switched to an active state by the ligand at a low concentration (Constantinescu et al., 2001). Both eJMC and TMC chimeras maintained the integrity of the capping region located at the C-terminal of the ectodomain, which has been proposed to be important for shielding the hydrophobic core of the LRR domain from the solvent (Forrer et al., 2003), and the external juxtamemembrane region, which transmits the ligand-induced conformational change (Moriki et al., 2001).

Characterization of the chimeras was first accomplished by in planta transient expression. Interestingly, whereas EFR and TMC did not show internalization in response to elf18 e flg22 respectively, eJMC, like FLS2 in *Arabidopsis*, showed internalization in response to flg22 in both *Arabidopsis* and tobacco. In the *Arabidopsis* bak1-4 mutant, where response to flg22 is almost abolished and response to elf18 is impaired (Chinchilla et al., 2007), the authors observed internalization of eJM as in the WT. The authors also observed that internalization requires the tetrapeptide YXXΦ present in EFR kinase domain, as the mutant eJMC$^{Y849A}$ was unable to leave the plasma membrane after stimulation.

Ethylene production, a typical EFR-related response, was induced at a similar extent upon stimulation of eJMC and more strongly upon activation of eJMC$^{Y849A}$. Ethylene production was instead hardly induced in elicited TMC- or FLS2-expressing tissues. The observation that activated EFR does not internalize, while eJMC does, similarly to FLS2, indicates that the lack of internalization is not due to the absence of appropriate targeting signals in EFR and suggests that it depends on the affinity characteristics of the interaction between elf18 and the EFR ectodomain. Furthermore, the strong ethylene response observed with eJMC$^{Y849A}$ indicates that internalization is not a requisite for eJMC signalling, but rather decreases the intensity of the response, in agreement with the notion that receptor endocytosis is often accompanied by degradation (Robatzek et al., 2006; Henriksen et al., 2008; Roepstorff et al., 2008; Chen 2009). Stable expression of the chimera eJMC in *Arabidopsis* ecotype Wassilewskija (Ws-0), which lacks FLS2 and does not respond to flg22, produced transgenic plants showing $H_2O_2$ production, callose deposition and defense gene expression in response to fgl22 as well as the ability to restrict *Pseudomonas syringae* colonization.

All in all, these data show that the eJMC is fully functional in both *Arabidopsis* and tobacco, where it confers the ability to perceive flg22.

EFR-Based Chimeric Receptors Reveal a Role of WAK1 as a Receptor of Oligogalacturonides In the second part of this work, the chimeric receptor approach based on EFR and the eJMC type of design was used to study whether WAK1 responds to OGs. The chimeras WEG and EWAK were constructed to characterize the ectodomain and kinase domain of WAK1, respectively. The WEG chimera, transiently expressed in tobacco leaves, showed internalization only in the presence of both OGs and EDTA, likely because the chelating agent, by sequestering $Ca^{++}$ and disrupting the "egg box" conformation of OGs and HGA (Cabrera et al., 2008), disanchors the receptor from the cell wall and allows internalization. Ethylene production, which does not occur in response to OGs in both *Arabidopsis* and tobacco (Ferrari et al., 2008) and present invention) was induced by OGs in WEG-expressing tissues, albeit at a level lower than that observed in EFR- or eJMC$^{Y849A}$-expressing tissues treated with elf18 and flg22, respectively. The weaker response of WEG may be intrinsic to the mode of signalling of OGs or due to the lower levels of expression of the chimera as compared to EFR or eJMC. Interestingly, a delay in the expression of a fluorescent WAK1 has been previously reported, likely due to its association with cell wall components in the cytoplasmic (Golgi) compartment to form detergent-insoluble complexes (Kohorn et al., 2006a).

Once demonstrated that the WAK1 ectodomain is able to perceive OGs and transmit the signal inside the cell, the next step of the present invention was to characterize the function of the WAK1 kinase domain. The EWAK chimera, upon treatment with elf18, produces a large oxidative burst and does not induce ethylene accumulation. Finally, since tobacco, like *N. benthamiana*, acquires responsiveness to elf18 only upon transient expression of EFR (see present FIG. 3F) and this receptor is known to reduce the extent of *A. tumefaciens* infection (Zipfel et al., 2006), the authors tested whether eWAK expression had a negative effect on bacterial colonization in agroinfiltrated tobacco tissues. No significant change in the number of colonizing bacteria was observed by infiltrating *Agrobacterium* carrying an empty vector (data not shown), the eJMC construct (in agreement with the notion that *Agrobacterium* flagellin is not recognized by the FLS2 ectodomain), WAK1 or WEG. By contrast, expression of either EFR or EWAK was associated to a 30% decrease of *Agrobacterium* colony number. This results indicates that elf18-mediated activation of the WAK1 kinase domain of EWAK triggers a defense response that affects bacterial survival. All in all, our results show that WAK1 is able of perceiving OGs and activating a signal transduction cascade leading to the activation of defense responses. This strongly supports the proposed role of the WAK receptor family in plant-pathogen interactions. In fact, it is known that WAK1 is induced by salicylic acid (Park et al., 2001), that overexpression of rice OsWAK1 enhances plant resistance against the blast fungus *Magnaporthe oryzae* (Li et al., 2009), and that WAKL22, which shares 45% identity and more than 65% of similarity with WAK1, is a dominant disease-resistance protein that confers resistance to a broad spectrum of *Fusarium* races [Resistance to *Fusarium oxysporium* 1 (RFO1); (Diener & Ausubel 2005)]. It is worth noting that WAK1 is the only member of the WAK family showing a significant induction of the corresponding transcript in response to OGs (about 2-fold at 1 and 3 h), and repression by flg22 (3 h). Therefore WAK1, similarly to what has been shown for FLS2 and EFR, is up-regulated upon perception of its own ligand.

The authors showed that constitutive expression of chimeric receptors confers resistance to both fungal and bacterial pathogens (*B. cinerea* for WEG plants; *P. syringae* for EWAK plants; *P. carotovorum* for WEG and EWAK plants), indicating the great potential of the present invention to confer broad-spectrum resistance.

In conclusion, the authors have shown the versatility of a chimeric receptor approach based on EFR. This approach, initially applied on LRR-RKs, allowed the characterization of WAK1, a non-LRR receptor kinase, as a receptor of OGs. The authors propose their chimeric receptor design for the characterization of the many plant receptors with no known function.

BIBLIOGRAPHY

Afzal A J, Wood A J, Lightfoot D A (2008) Mol Plant Microbe Interact 21: 507-517
Ali G S, Prasad K V, Day dI, Reddy A S (2007) Plant Cell Physiol 48: 1601-1611
Bauer et al., (2001) Journal of Biological Chemistry 276:45669-45676
Bellincampi D, et al., (1996) Plant Cell 8: 477-487
Bennasroune A, et al., (2005) Cell Mol Life Sci 62: 2124-2131
Bocharov E V, et al., (2008) J Biol Chem 283: 6950-6956
Boller T, Felix G. (2009) Annu Rev Plant Biol.; 60:379-406.
Brownlee C (2002) Curr Opin Plant Biol 5: 396-401
Cabrera J C, et al., (2008) Glycobiology 18: 473-482
Cao Y, Ding X, Cai M, Zhao J, Lin Y, Li X, Xu C, Wang S (2007a) Genetics 177: 523-533
Cao Y, et al., (2007b) Theor Appl Genet 115: 887-895
Casasoli M, et al., (2008) Proteomics 8: 1042-1054
Casasoli M et al. (2009) PNAS 106:7666-7671
Cervone F, et al., P (1989) In B J J Lugtenberg, ed Signal Molecules in Plants and Plant-Microbe Interactions. NATO ASI Series, Volume H36. Springer Verlag, Heidelberg, F R G, pp 85-89
Chen Y G (2009) Cell Res 19: 58-70
Chinchilla D, et al., (2007) Nature 448: 497-500
Constantinescu S N, et al., (2001) PNAS 98: 4379-4384
Decreux A, Messiaen J (2005) Plant Cell Physiol 46: 268-278
Denoux C, et al., (2008) Molecular Plant 1: 423-445
Diener A C, Ausubel F M (2005) Genetics 171: 305-321
Ferrari S, et al., (2007) Plant Physiol 144: 367-379
Ferrari S, et al., (2008) Plant Physiol 146: 669-681
Forrer P, Stumpp M T, Binz H K, Pluckthun A (2003) FEBS Lett 539: 2-6
Galletti R et al. (2008) Plant Physiol 148:1695-1706
Gardan L., et al., 2003. Int J System Evol Microbiol 53: 381-391.
Geldner N, Robatzek S (2008) Plant Physiol 147: 1565-1574
Gomez-Gomez L, et al., (1999) Plant J. 18:277-284
Hammond D E, Urbe S, Woude G F V, Clague M J (2001) Oncogene 20: 2761-2770
He Z, Wang Z Y, Li J, Zhu Q, Lamb C, Ronald P, Chory J (2000) Science 288: 2360-2363
He Z H, Fujiki M, Kohorn B D (1996) J Biol Chem 271: 19789-19793
He Z H, He D Z, Kohorn B D (1998) Plant Journal 14: 55-63
Henriksen L, et al., (2008) Apmis 116: 431
Husebye H, et al., (2006) EMBO J 25: 683-692
Jemth P, Gianni S, (2007) Biochemistry 46(30):8701-8.
Jiang D, et al., (2007) Annual Review of Cell and Developmental Biology 23:435-461
Kohorn B D (2000) Plant Physiol 124: 31-38
Kohorn B D, et al., (2006a) J Cell Sci 119: 2282-2290
Kohorn B D, et al., (2006b) Plant Journal 46: 307-316
Lacombe D, et al., (2010) Nature Biotechnology 28:365-369
Lally D, Ingmire P, Tong H Y, He Z H (2001) Plant Cell 13: 1317-1331
Larkin M. A., et al., (2007) Bioinformatics 23(21): 2947-2948.
Li H, Zhou S Y, Zhao W S, Su S C, Peng Y L (2009) Plant Mol Biol, in press
Lord E M (2003) Journal of Experimental Botany 54: 47-54
Mauro M L, De Lorenzo G, Costantino P, Bellincampi D (2002) Planta 215: 494-501
Mendrola J M, Berger M B, King M C, Lemmon M A (2002) J Biol Chem 277: 4704-4712
Micheli F (2001) Trends Plant Sci 6: 414-419
Moriki T, Maruyama H, Maruyama I N (2001) J Mol Biol 311: 1011-1026
Nam K H, Li J (2002) Cell 110: 203-212
Oh M H, et al., (2000) Plant Physiol 124: 751-766
Park A R, et al., (2001) J Biol Chem 276: 26688-26693
Pilling J, Willmitzer L, Bucking H, Fisahn J (2004) Planta 219: 32-40
Rairdan G J, Moffett P (2006) Plant Cell 18: 2082-2093
Reca I B, et al., (2008) Biochimie 90: 1611-1623
Ridley B L, O'Neill M A, Mohnen D (2001) Phytochemistry 57: 929-967
Robatzek S, et al., (2007) Plant Mol Biol 64: 539-547
Robatzek S, Chinchilla D, Boller T (2006) Genes Dev 20: 537-542
Roepstorff K, et al., (2008) Histochem Cell Biol 129: 563-578
Sanabria N, Goring D, Nurnberger T, Dubery I (2008) New Phytol 178: 503-513
Shiu SH, et al., (2004) Plant Cell 16: 1220-1234
Spadoni S, et al., (2006) Plant Physiol 141: 557-564
Stenzel I, et al., (2008) Plant Cell 20: 124-141
Stern R, Asari A A, Sugahara K N (2006) Eur J Cell Biol 85: 699-715
Tauszig S, et al., (2000) Proc Natl Acad Sci USA 97: 10520-10525
Taylor K R, Gallo R L (2006) FASEB J 20: 10-20
Tsujita T, et al., (2004) J Biol Chem 279: 48588-48597

Van der Hoorn R A, et al., (2005) Plant Cell 17: 1000-1015

Verica J A, Chae L, Tong H Y, Ingmire P, He Z H (2003) Plant Physiol 133: 1732-1746

Verica J A, He Z H (2002) Plant Physiol 129: 455-459

Vorwerk S, Somerville S, Somerville C (2004) Trends Plant Sci 9: 203-209

Wagner T A, Kohorn B D (2001) Plant Cell 13: 303-318

Weber A N, et al., (2005) J Biol Chem 280: 22793-22799

Wulff B B, Thomas C M, Smoker M, Grant M, Jones J D (2001) Plant Cell 13: 255-272

Zipfel C (2008) Curr Opin Immunol 20: 10-16

Zipfel C, et al., (2006) Cell 125: 749-760

Zipfel C, et al., (2004) Nature 428: 764-767

The invention claimed is:

1. A polynucleotide construct encoding a chimeric receptor comprising:
   a) an extracellular portion R1 selected from the group consisting of
      i) Flagellin Sensing 2 Receptor (FLS2) amino acid residues 1 through 806 of SEQ ID NO: 30,
      ii) Elongation Factor Tu Receptor (EFR) amino acid residues 1 through 649 of SEQ ID NO: 31, and
      iii) Wall Associated Kinase 1 Receptor (WAK1) amino acid residues 1 through 333 of SEQ ID NO: 32; and
   b) a transmembrane portion joined to an intracellular portion R2 wherein R2 is selected from the group consisting of
      iv) EFR amino acid residues 650 through 1031 of SEQ ID NO: 31, and
      v) WAK1 amino acid residues 334 to 735 of SEQ ID NO: 32;
   and wherein R1 and R2 are from different proteins.

2. The construct according to claim 1, wherein said R1 is able to recognize a ligand released or produced during an infection of a plant by phytophathogens.

3. The construct according to claim 1, wherein the transmembrane portion and the intracellular portion R2, of the chimeric receptor, comprising the internal juxtamembrane region of EFR, is fused with R1, that consists of amino acid residues 1 through 333 of SEQ ID NO: 32.

4. The construct according to claim 1, wherein the transmembrane portion and the intracellular portion R2, of the chimeric receptor, comprising the internal juxtamembrane region of WAK1, is fused with R1, that consists of amino acid residues 1 through 649 of SEQ ID NO: 31.

5. A plant transformed with the construct according to claim 1.

6. A plant according to claim 5, that is resistant to fungal and/or bacterial pathogens.

7. The construct according to claim 1, wherein the transmembrane portion and the intracellular portion R2, of the chimeric receptor, comprising the internal juxtamembrane region of EFR, is fused with R1, that consists of amino acid residues 1 through 806 of SEQ ID NO: 30.

* * * * *